United States Patent
Jain et al.

(10) Patent No.: US 9,226,907 B2
(45) Date of Patent: *Jan. 5, 2016

(54) EXTENDED RELEASE HYDROCODONE ACETAMINOPHEN AND RELATED METHODS AND USES THEREOF

(75) Inventors: Rita I. Jain, Evanston, IL (US); Andrea E. Best, Lake Forest, IL (US); Earle Lockhart, Lake Bluff, IL (US); Steven E. Marx, Hoffman Estates, IL (US); James W. Thomas, Grayslake, IL (US); Pamela Giang Vo, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 157 days.

This patent is subject to a terminal disclaimer.

(21) Appl. No.: 12/365,639

(22) Filed: Feb. 4, 2009

(65) Prior Publication Data

US 2010/0010030 A1  Jan. 14, 2010

Related U.S. Application Data

(60) Provisional application No. 61/092,907, filed on Aug. 29, 2008, provisional application No. 61/028,053, filed on Feb. 12, 2008, provisional application No. 61/025,587, filed on Feb. 1, 2008.

(51) Int. Cl.
  *A61K 31/44* (2006.01)
  *A61K 31/165* (2006.01)
  *A61K 31/439* (2006.01)

(52) U.S. Cl.
  CPC .............. *A61K 31/165* (2013.01); *A61K 31/439* (2013.01)

(58) Field of Classification Search
  USPC ........................................................ 514/282
  See application file for complete search history.

(56) References Cited

U.S. PATENT DOCUMENTS

| | | |
|---|---|---|
| 2,799,241 A | 7/1957 | Wurster |
| 3,133,132 A | 5/1964 | Loeb et al. |
| 3,173,876 A | 3/1965 | Zobrist |
| 3,276,586 A | 10/1966 | Rosaen |
| 3,480,616 A | 11/1969 | Osipow et al. |
| 3,541,005 A | 11/1970 | Strathmann et al. |
| 3,541,006 A | 11/1970 | Bixler et al. |
| 3,546,142 A | 12/1970 | Michaels et al. |
| 3,845,770 A | 11/1974 | Theeuwes et al. |
| 3,865,108 A | 2/1975 | Hartop |
| 3,916,899 A | 11/1975 | Theeuwes et al. |
| 3,980,766 A | 9/1976 | Shaw et al. |
| 3,995,631 A | 12/1976 | Higuchi et al. |
| 4,002,173 A | 1/1977 | Manning et al. |
| 4,034,756 A | 7/1977 | Higuchi et al. |
| 4,063,064 A | 12/1977 | Saunders et al. |
| 4,070,494 A | 1/1978 | Hoffmeister et al. |
| 4,077,407 A | 3/1978 | Theeuwes et al. |
| 4,088,864 A | 5/1978 | Theeuwes et al. |
| 4,111,202 A | 9/1978 | Theeuwes |
| 4,160,020 A | 7/1979 | Ayer et al. |
| 4,200,098 A | 4/1980 | Ayer et al. |
| 4,207,893 A | 6/1980 | Michaels |
| 4,285,987 A | 8/1981 | Ayer et al. |
| 4,320,759 A | 3/1982 | Theeuwes |
| 4,327,725 A | 5/1982 | Cortese et al. |
| 4,449,983 A | 5/1984 | Cortese et al. |
| 4,519,801 A | 5/1985 | Edgren |
| 4,578,075 A | 3/1986 | Urquhart et al. |
| 4,681,583 A | 7/1987 | Urquhart et al. |
| 4,765,989 A | 8/1988 | Wong et al. |
| 4,820,522 A | 4/1989 | Radebaugh et al. |
| 4,834,984 A | 5/1989 | Goldie et al. |
| 4,844,909 A | 7/1989 | Goldie et al. |
| 4,892,778 A | 1/1990 | Theeuwes et al. |
| 4,940,465 A | 7/1990 | Theeuwes et al. |
| 4,968,509 A | 11/1990 | Radebaugh et al. |
| 4,990,341 A | 2/1991 | Goldie et al. |
| 5,004,613 A | 4/1991 | Radebaugh et al. |
| 5,019,397 A | 5/1991 | Wong et al. |
| 5,156,850 A | 10/1992 | Wong et al. |
| 5,266,331 A | 11/1993 | Oshlack et al. |

(Continued)

FOREIGN PATENT DOCUMENTS

| | | |
|---|---|---|
| EP | 151702 A2 | 8/1985 |
| EP | 249347 A2 | 12/1987 |

(Continued)

OTHER PUBLICATIONS

OPANA ER—dailymed.nih.gov/dailymed/fdaDrugXsl.cfm?id (2007) 37 pages.*
Zhang et al. (Ann Rheum Dis 2004;63:901-907).*
Rubin (JAOA Supplement 4 vol. 105 ( 9) Sep. 2005 S23-S28).*
Barkin, R.L., "Acetaminophen, Aspirin, or Ibuprofen in Combination Analgesic Products," American Journal of Therapeutics, 2001, 433-442, vol. 8.
Beaver, W. T. et al., "Methodological considerations in the evaluation of analgesic combinations: acetaminophen (paracetamol) and hydrocodone in postpartum pain, XP002527609," British Journal of Clinical Pharmacology, vol. 10 Suppl 2, pp. 215S-223S , 1980.
Cao, Qing-Ri, "Formulation, release characteristics and bioavailability of novel monolithic hydroxypropylmethylcellulose matrix tablets containing acetaminophen," Journal of Controlled Release, 2005, 351-361, vol. 108—Issue 2-3.

(Continued)

Primary Examiner — Shirley V Gembeh
(74) Attorney, Agent, or Firm — Lisa V. Mueller; Michael Best & Friedrich LLP

(57) ABSTRACT

The present invention generally provides a method of treatment and improvement of quality of life for patients adversely affected by various pain conditions. One preferred embodiment provides a method of treatment of acute pain, moderate to moderately severe pain, chronic pain, non-cancer pain, osteoarthritic pain, bunionectomy pain or lower back pain in a patient in need thereof, comprising providing at least one or two dosage form having about 15 mg of hydrocodone and its salt and about 500 mg of acetaminophen, once, twice or thrice daily. Preferably, the dosage form is about 30 mg of hydrocodone and about 1000 mg of acetaminophen taken twice daily. Alternatively, the dosage form is about 15 mg of hydrocodone and about 500 mg of acetaminophen taken twice daily.

5 Claims, 14 Drawing Sheets

(56) References Cited

U.S. PATENT DOCUMENTS

| | | |
|---|---|---|
| 5,451,409 A | 9/1995 | Rencher et al. |
| 5,460,826 A | 10/1995 | Merrill et al. |
| 5,500,227 A | 3/1996 | Oshlack et al. |
| 5,508,042 A | 4/1996 | Oshlack et al. |
| 5,529,787 A | 6/1996 | Merrill et al. |
| 5,549,912 A | 8/1996 | Oshlack et al. |
| 5,593,695 A | 1/1997 | Merrill et al. |
| 5,656,295 A | 8/1997 | Oshlack et al. |
| 5,702,725 A | 12/1997 | Merrill et al. |
| 5,773,031 A | 6/1998 | Shah et al. |
| 5,866,161 A | 2/1999 | Childers et al. |
| 5,866,164 A | 2/1999 | Kuczynski et al. |
| 5,912,268 A | 6/1999 | Guittard et al. |
| 5,914,131 A | 6/1999 | Merrill et al. |
| 5,948,787 A | 9/1999 | Merrill et al. |
| 5,958,452 A | 9/1999 | Oshlack et al. |
| 5,958,459 A | 9/1999 | Chasin et al. |
| 5,965,161 A | 10/1999 | Oshlack et al. |
| 6,077,538 A | 6/2000 | Merrill et al. |
| 6,090,411 A | 7/2000 | Pillay et al. |
| 6,103,261 A | 8/2000 | Chasin et al. |
| 6,126,969 A | 10/2000 | Shah et al. |
| 6,132,420 A | 10/2000 | Dionne et al. |
| 6,143,322 A | 11/2000 | Sackler et al. |
| 6,159,501 A | 12/2000 | Skinhoj |
| 6,228,863 B1 | 5/2001 | Palermo et al. |
| 6,245,357 B1 | 6/2001 | Edgren et al. |
| 6,251,430 B1 | 6/2001 | Zhang et al. |
| 6,261,599 B1 | 7/2001 | Oshlack et al. |
| 6,264,891 B1 | 7/2001 | Heyneker et al. |
| 6,270,787 B1 | 8/2001 | Ayer |
| 6,277,384 B1 | 8/2001 | Kaiko et al. |
| 6,283,953 B1 | 9/2001 | Ayer et al. |
| 6,284,274 B1 | 9/2001 | Merrill et al. |
| 6,287,295 B1 | 9/2001 | Chen et al. |
| 6,294,195 B1 | 9/2001 | Oshlack et al. |
| 6,309,668 B1 | 10/2001 | Bastin et al. |
| 6,315,720 B1 | 11/2001 | Williams et al. |
| 6,316,031 B1 | 11/2001 | Oshlack et al. |
| 6,333,050 B2 | 12/2001 | Wong et al. |
| 6,335,033 B2 | 1/2002 | Oshlack et al. |
| 6,337,091 B1 | 1/2002 | Kim et al. |
| 6,342,249 B1 | 1/2002 | Wong et al. |
| 6,350,398 B1 | 2/2002 | Breitenbach et al. |
| 6,361,794 B1 | 3/2002 | Kushla et al. |
| 6,368,626 B1 | 4/2002 | Bhatt et al. |
| 6,375,957 B1 | 4/2002 | Kaiko et al. |
| 6,375,978 B1 | 4/2002 | Kleiner et al. |
| 6,387,404 B2 | 5/2002 | Oshlack et al. |
| 6,475,494 B2 | 11/2002 | Kaiko et al. |
| 6,485,748 B1 | 11/2002 | Chen et al. |
| 6,491,683 B1 | 12/2002 | Dong et al. |
| 6,491,945 B1 | 12/2002 | Childers et al. |
| 6,495,162 B2 | 12/2002 | Cheng et al. |
| 6,572,885 B2 | 6/2003 | Oshlack et al. |
| 6,589,960 B2 | 7/2003 | Harclerode et al. |
| 6,627,635 B2 | 9/2003 | Palermo et al. |
| 6,696,066 B2 | 2/2004 | Kaiko et al. |
| 6,706,281 B2 | 3/2004 | Oshlack et al. |
| 6,730,321 B2 | 5/2004 | Ting et al. |
| 6,733,783 B2 | 5/2004 | Oshlack et al. |
| 6,743,442 B2 | 6/2004 | Oshlack et al. |
| 6,806,294 B2 | 10/2004 | Wimmer et al. |
| 2001/0008639 A1 | 7/2001 | Oshlack et al. |
| 2001/0012847 A1 | 8/2001 | Lam et al. |
| 2001/0031278 A1 | 10/2001 | Oshlack et al. |
| 2001/0033865 A1 | 10/2001 | Oshlack et al. |
| 2001/0036476 A1 | 11/2001 | Oshlack et al. |
| 2002/0004509 A1 | 1/2002 | Palermo et al. |
| 2002/0006438 A1 | 1/2002 | Oshlack et al. |
| 2002/0013301 A1 | 1/2002 | Kaiko et al. |
| 2002/0018810 A1 | 2/2002 | Oshlack et al. |
| 2002/0058673 A1 | 5/2002 | Kaiko et al. |
| 2002/0081333 A1 | 6/2002 | Oshlack et al. |
| 2002/0102303 A1 | 8/2002 | Oshlack et al. |
| 2002/0164371 A1 | 11/2002 | Ting et al. |
| 2002/0164373 A1 | 11/2002 | Maloney |
| 2002/0165248 A1 | 11/2002 | Wimmer et al. |
| 2002/0187192 A1 | 12/2002 | Joshi et al. |
| 2002/0192277 A1 | 12/2002 | Oshlack et al. |
| 2003/0018036 A1 | 1/2003 | Westbrook et al. |
| 2003/0026839 A1 | 2/2003 | Oshlack et al. |
| 2003/0031712 A1 | 2/2003 | Kaiko et al. |
| 2003/0054032 A1 | 3/2003 | Oshlack et al. |
| 2003/0064099 A1 | 4/2003 | Oshlack et al. |
| 2003/0068370 A1 | 4/2003 | Sackler |
| 2003/0068375 A1 | 4/2003 | Wright et al. |
| 2003/0077320 A1 | 4/2003 | Childers et al. |
| 2003/0092724 A1 | 5/2003 | Kao et al. |
| 2003/0099704 A1 | 5/2003 | Oshlack et al. |
| 2003/0118641 A1 | 6/2003 | Maloney et al. |
| 2003/0129230 A1 | 7/2003 | Baichwal et al. |
| 2003/0129231 A1 | 7/2003 | Oshlack et al. |
| 2003/0157168 A1 | 8/2003 | Breder et al. |
| 2003/0180361 A1 | 9/2003 | Oshlack et al. |
| 2003/0180362 A1 | 9/2003 | Park et al. |
| 2003/0190358 A1 | 10/2003 | Oshlack et al. |
| 2003/0190362 A1 | 10/2003 | Sackler et al. |
| 2003/0224051 A1 | 12/2003 | Fink et al. |
| 2004/0042964 A1 | 3/2004 | Joshi et al. |
| 2004/0047907 A1 | 3/2004 | Oshlack et al. |
| 2004/0052731 A1 | 3/2004 | Hirsh et al. |
| 2004/0058946 A1 | 3/2004 | Buchwald et al. |
| 2004/0062812 A1 | 4/2004 | Maloney |
| 2004/0081694 A1 | 4/2004 | Oshlack et al. |
| 2004/0086461 A1 | 5/2004 | Kohn et al. |
| 2004/0086563 A1 | 5/2004 | Fanara et al. |
| 2004/0170680 A1 | 9/2004 | Oshlack et al. |
| 2004/0185096 A1 | 9/2004 | Oshlack et al. |
| 2004/0202716 A1 | 10/2004 | Chan et al. |
| 2004/0202717 A1 | 10/2004 | Mehta |
| 2004/0224020 A1 | 11/2004 | Schoenhard |
| 2004/0228802 A1 | 11/2004 | Chang et al. |
| 2004/0228924 A1 | 11/2004 | Oshlack et al. |
| 2004/0234600 A1 | 11/2004 | Merrill et al. |
| 2004/0253310 A1 | 12/2004 | Fischer et al. |
| 2004/0266807 A1 | 12/2004 | Oshlack et al. |
| 2005/0020613 A1 | 1/2005 | Boehm et al. |
| 2005/0031246 A1 | 2/2005 | Rowe |
| 2005/0031546 A1 | 2/2005 | Bartholomaus et al. |
| 2005/0074493 A1 | 4/2005 | Mehta et al. |
| 2005/0089568 A1 | 4/2005 | Oshlack et al. |
| 2005/0089570 A1 | 4/2005 | Cruz et al. |
| 2005/0095299 A1 | 5/2005 | Wynn et al. |
| 2005/0112195 A1 | 5/2005 | Cruz et al. |
| 2005/0152843 A1 | 7/2005 | Bartholomaus et al. |
| 2005/0158382 A1 | 7/2005 | Cruz et al. |
| 2005/0163856 A1 | 7/2005 | Maloney et al. |
| 2005/0192309 A1 | 9/2005 | Palermo et al. |
| 2005/0226929 A1 | 10/2005 | Xie et al. |
| 2005/0232987 A1 | 10/2005 | Srinivasan et al. |
| 2005/0266072 A1 | 12/2005 | Oshlack et al. |
| 2005/0271594 A1 | 12/2005 | Groenewoud |
| 2005/0281748 A1 | 12/2005 | Hirsh et al. |
| 2005/0287211 A1 | 12/2005 | Yoshida et al. |
| 2006/0002859 A1 | 1/2006 | Arkenau et al. |
| 2006/0002860 A1 | 1/2006 | Bartholomaus et al. |
| 2006/0051298 A1 | 3/2006 | Groenewoud |
| 2006/0057210 A1 | 3/2006 | Oshlack et al. |
| 2006/0062809 A1 | 3/2006 | Six et al. |
| 2006/0062847 A1 | 3/2006 | Kolter et al. |
| 2006/0099255 A1 | 5/2006 | Oshlack et al. |
| 2006/0104909 A1 | 5/2006 | Vaghefi et al. |
| 2006/0110327 A1 | 5/2006 | Emigh et al. |
| 2006/0165790 A1 | 7/2006 | Walden et al. |
| 2007/0281018 A1 | 12/2007 | Qiu et al. |

FOREIGN PATENT DOCUMENTS

| | | |
|---|---|---|
| EP | 271193 A2 | 6/1988 |
| EP | 305051 A1 | 3/1989 |
| EP | 576643 A1 | 1/1994 |
| EP | 631781 A1 | 1/1995 |
| EP | 636370 A1 | 2/1995 |

(56) References Cited

FOREIGN PATENT DOCUMENTS

| | | |
|---|---|---|
| EP | 722730 A1 | 7/1996 |
| EP | 742711 A1 | 11/1996 |
| EP | 785775 A1 | 7/1997 |
| EP | 864325 A2 | 9/1998 |
| EP | 888111 A1 | 1/1999 |
| EP | 1041987 A1 | 10/2000 |
| EP | 1059916 A1 | 12/2000 |
| EP | 1109540 A1 | 6/2001 |
| EP | 1121109 A2 | 8/2001 |
| EP | 1243269 A2 | 9/2002 |
| EP | 1258246 A2 | 11/2002 |
| EP | 1325746 A1 | 7/2003 |
| EP | 1327445 A1 | 7/2003 |
| EP | 1327446 A1 | 7/2003 |
| EP | 1348429 A2 | 10/2003 |
| EP | 1384471 A1 | 1/2004 |
| EP | 1404331 A1 | 4/2004 |
| EP | 1430897 A2 | 6/2004 |
| EP | 1438959 A1 | 7/2004 |
| EP | 1449530 A2 | 8/2004 |
| EP | 1449531 A2 | 8/2004 |
| EP | 1475085 A1 | 11/2004 |
| EP | 1488786 A1 | 12/2004 |
| EP | 1504758 A2 | 2/2005 |
| EP | 1553229 A1 | 7/2005 |
| EP | 1600154 A1 | 11/2005 |
| EP | 1623703 A1 | 2/2006 |
| EP | 1502592 B1 | 6/2007 |
| WO | WO-9004965 A1 | 5/1990 |
| WO | WO-9310765 A1 | 6/1993 |
| WO | WO-9317673 A1 | 9/1993 |
| WO | WO-9405257 A1 | 3/1994 |
| WO | WO-9520947 A1 | 8/1995 |
| WO | WO-9601629 A1 | 1/1996 |
| WO | WO-9614058 A1 | 5/1996 |
| WO | WO-9732573 A1 | 9/1997 |
| WO | WO-9745091 A2 | 12/1997 |
| WO | WO-9806380 A2 | 2/1998 |
| WO | WO-9814168 A2 | 4/1998 |
| WO | WO-9921551 A1 | 5/1999 |
| WO | WO-9932119 A1 | 7/1999 |
| WO | WO-9932120 A1 | 7/1999 |
| WO | WO-9939698 A1 | 8/1999 |
| WO | WO-9944591 A1 | 9/1999 |
| WO | WO-9945887 A2 | 9/1999 |
| WO | WO-9962496 A1 | 12/1999 |
| WO | WO-0013678 A1 | 3/2000 |
| WO | WO-0018378 A1 | 4/2000 |
| WO | WO-0021520 A2 | 4/2000 |
| WO | WO-0041481 A2 | 7/2000 |
| WO | WO-0108661 A2 | 2/2001 |
| WO | WO-0108665 A1 | 2/2001 |
| WO | WO-0132148 A1 | 5/2001 |
| WO | WO-0176562 A1 | 10/2001 |
| WO | WO-0180834 A1 | 11/2001 |
| WO | WO-0236099 A1 | 5/2002 |
| WO | WO-02087512 A2 | 11/2002 |
| WO | WO-02087558 A1 | 11/2002 |
| WO | WO-03004033 A1 | 1/2003 |
| WO | WO-03013476 A1 | 2/2003 |
| WO | WO-03024430 A1 | 3/2003 |
| WO | WO-03049741 A1 | 6/2003 |
| WO | WO-03063834 A1 | 8/2003 |
| WO | WO-03072083 A2 | 9/2003 |
| WO | WO-03082204 A2 | 10/2003 |
| WO | WO-03092648 A1 | 11/2003 |
| WO | WO-03101384 A2 | 12/2003 |
| WO | WO-03105808 A1 | 12/2003 |
| WO | WO-2004004683 A1 | 1/2004 |
| WO | WO-2004004693 A1 | 1/2004 |
| WO | WO-2004006904 A1 | 1/2004 |
| WO | WO-2004026256 A2 | 4/2004 |
| WO | WO-2004026262 A2 | 4/2004 |
| WO | WO-2004056337 A2 | 7/2004 |
| WO | WO-2004084868 A1 | 10/2004 |
| WO | WO-2004091512 A2 | 10/2004 |
| WO | WO-2004093801 A2 | 11/2004 |
| WO | WO-2004093819 A2 | 11/2004 |
| WO | WO-2004100894 A2 | 11/2004 |
| WO | WO-2005000310 A1 | 1/2005 |
| WO | WO-2005007135 A1 | 1/2005 |
| WO | WO-2005030166 A1 | 4/2005 |
| WO | WO-2005030181 A1 | 4/2005 |
| WO | WO-2005030182 A1 | 4/2005 |
| WO | WO-2005032555 A2 | 4/2005 |
| WO | WO-2005034859 A2 | 4/2005 |
| WO | WO-2005041968 A2 | 5/2005 |
| WO | WO-2005044230 A2 | 5/2005 |
| WO | WO-2005055981 A2 | 6/2005 |
| WO | WO-2005065639 A2 | 7/2005 |
| WO | WO-2005072079 A2 | 8/2005 |
| WO | WO-2005079760 A1 | 9/2005 |
| WO | WO-2005105045 A1 | 11/2005 |
| WO | WO-2005123039 A1 | 12/2005 |
| WO | WO-2006002808 A2 | 1/2006 |
| WO | WO-2006024881 A2 | 3/2006 |
| WO | WO-2006028830 A2 | 3/2006 |
| WO | WO-2006051704 A1 | 5/2006 |
| WO | WO-2006058249 A2 | 6/2006 |
| WO | WO-2006079550 A2 | 8/2006 |
| WO | WO-2006087218 A1 | 8/2006 |
| WO | WO-2007085024 A3 | 7/2007 |
| WO | WO-2007103113 A2 | 9/2007 |
| WO | WO-2008011169 A2 | 1/2008 |

OTHER PUBLICATIONS

Donbrow and Friedman, "Enhancement of Permeability of Ethyl Cellulose Films for Drug Penetration," J.Pharm. Pharmacol. 1975, 633-646, vol. 27.

Donbrow and Samuelov, "Zero Order Drug Delivery from Double-Layered Porous Films: Release Rate Profiles fro Ethyl Cellulose, Hydroxypropyl cellulose and polyethylene glycol mixtures," J.Pharm. Pharmacol. 1980, 463-470, vol. 32.

European Patent Office, International Application No. PCT/US2007/073957, International Search Report, May 26, 2008 (Completion Date of the International Search: May 13, 2008).

Gimbel, J.S. et al., "Efficacy and Tolerability of Celecoxib Versus Hydrocodone/Acetaminophen in the Treatment of Pain After Ambulatory Orthopedic Surgery in Adults," Clin Therap, 2001, 228-241, vol. 23—Issue 2.

Glaxosmithkline "Submission to the Medicines Classification Committee for Reclassification of a Medicine," SamithKline Beecham, 2001, 101-103, vol. 1.

Higuchi, T. "Rate of Release of Medicaments from Ointment Bases Cointaining Drugs in Suspension," J.of Pharm Sci. 1961, 874-875, vol. 50.

International Search Report for application No. PCT/EP09/050853, Mailed on Apr. 28, 2009, 3 pages.

Interscience Publishers, "Cellulose Eters, Organic", Encyl. of Polymer Sci. & Tech., 3:325-324 (1964).

Perry, Green & Maloney Editors, et al., "Introduction to Screening and Wet Classification, Perry's Chemical Engineers Handbook," 1984, 21.13 to 21.19, 6th Ed.

Ripple, E.G., "Powders," 1985, 1585-1594, 89, Mack Publishing, Chapt.

Roth W et al., "Ethanol effects on drug release from Verapami 1 Mel trex, an innovative melt extruded formulation," International Journal of Pharmaceutics, 368 (1-2), 72-75, 2009.

Rowe R.C. "The effect of the molecular weight of ethyl cellulose on the drug release properties of mixed films of ethyl cellulose and hydroxypropyl methylcellulose," International Journal of Pharmaceutics, 1986, 37-41, vol. 29.

Santus G. & Baker R.W. "Osmotic drug delivery: a review of the patent literature," Journal of Controlled Release, 1995, 1-21, vol. 35.

Wurster, D.E. "Air-Suspension Technique of Coating Drug Particles," Journal of American Pharmaceutical Association, 1959, 451-459, vol. 48.

* cited by examiner

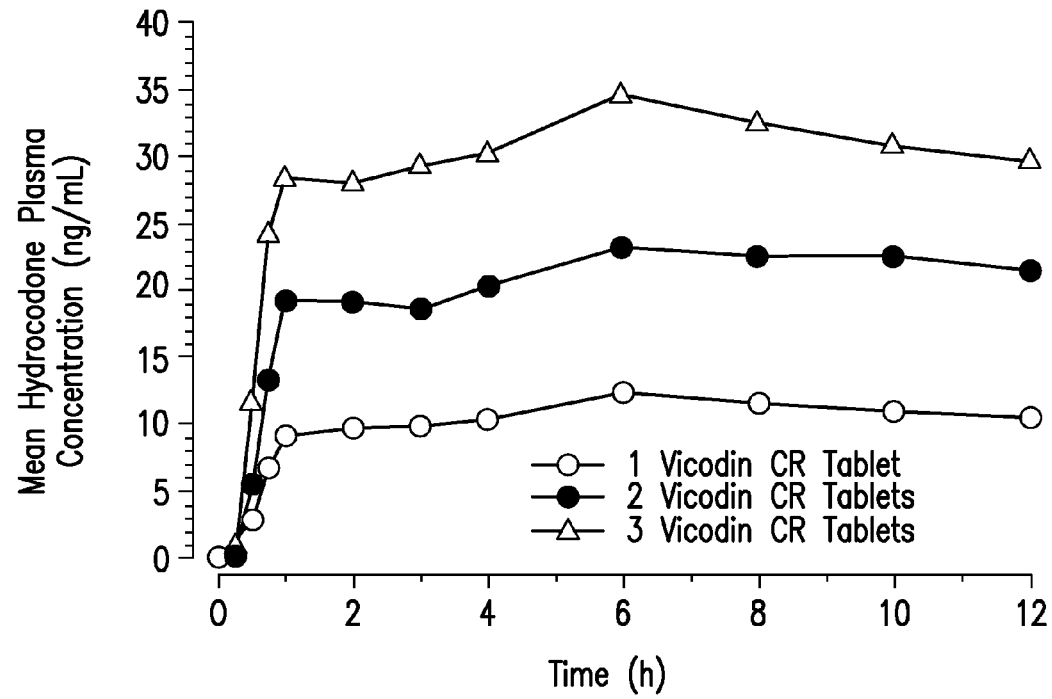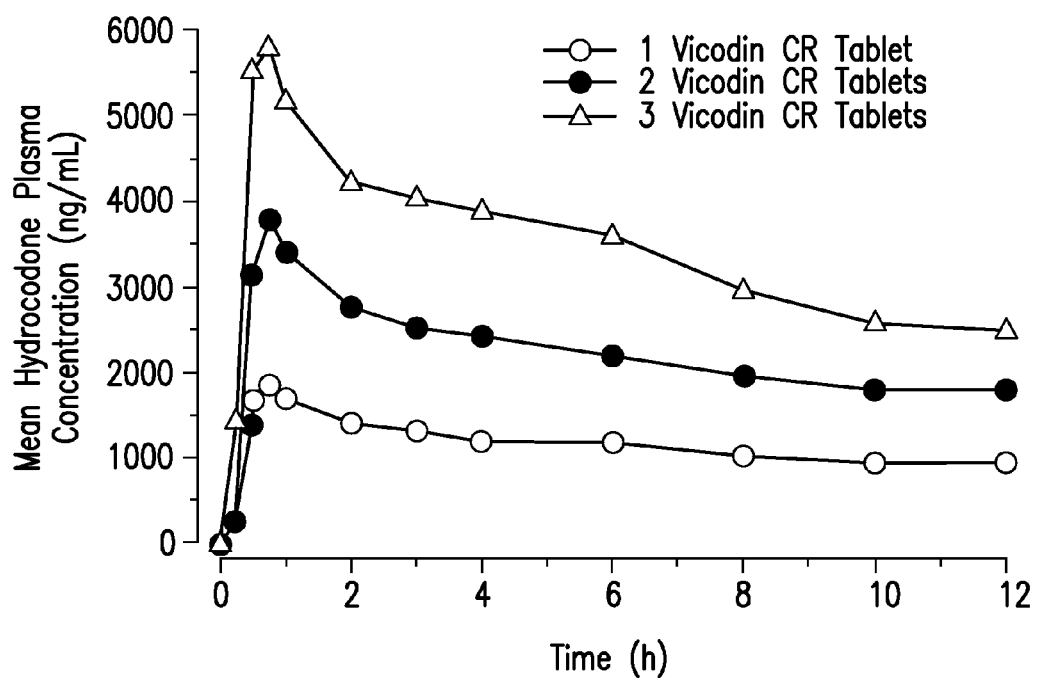
FIG.2

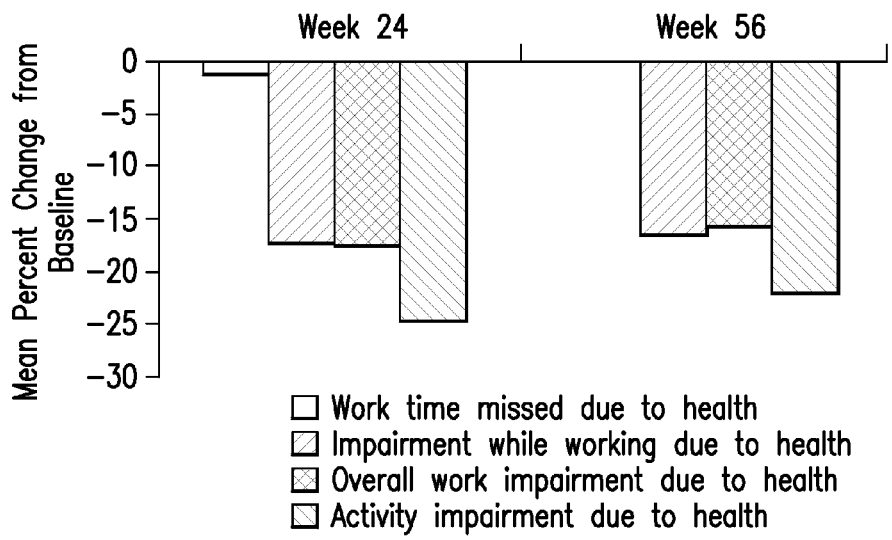

| Washout | Titration<br>–1 wk– | Maintenance<br>–56 wks– | Taper<br>–1 wk– | Follow up<br>–1 wk– |
|---|---|---|---|---|
| | HC/APAP CR<br>1 Tab qd x 3d;<br>1 Tab bid x 4d | HC/APAP CR<br>2 Tabs bid | HC/APAP CR<br>1 Tab bid x 4d;<br>1 Tab qd x 3d | |

Screening Visit — Baseline — Wk 0 — Wk 56 — Wk 57 — Wk 58

WPAI: Baseline — Wk 24 — Wk 56

HC/APAP CR cr = extended-release hydrocodone/acetaminophen;
Tab = tablet; qd = once daily; bid = twice daily; wk = week
Scheduled study visits during the maintenance period took place
at wk 2 and every 4 wks from wk 4 through wk 56.

| Washout | Titration<br>–1 wk– | Maintenance<br>–56 wks– | Taper<br>–1 wk– | Follow up<br>–1 wk– |
|---|---|---|---|---|
| | HC/APAP CR<br>1 Tab qd x 3d;<br>1 Tab bid x 4d | HC/APAP CR<br>2 Tabs bid | HC/APAP CR<br>1 Tab bid x 4d;<br>1 Tab qd x 3d | |

Screening Visit | Baseline | Wk 0 | Wk 56 | Wk 57 | Wk 58

SF-36 & WPAI: Baseline — Wk 24, Wk 56

BPI: Baseline — Wk 4, Wk 12, Wk 24, Wk 40, Wk 56

HC/APAP CR = extended-release hydrocodone/acetaminophen;
Tab = tablet; qd = once daily; bid = twice daily; wk = week
Scheduled study visits during the maintenance period took place
at wk 2 and every 4 wks from wk 4 through wk 56.

FIG. 10

Note: Pain Intensity Scale: 0-10 (11-point scale, 0 = no pain, 10 = pain as bad as you can imagine). Pain interference scale: 0-10 (11-point scale, 0 = does not interfere, 10 = completely interferes).

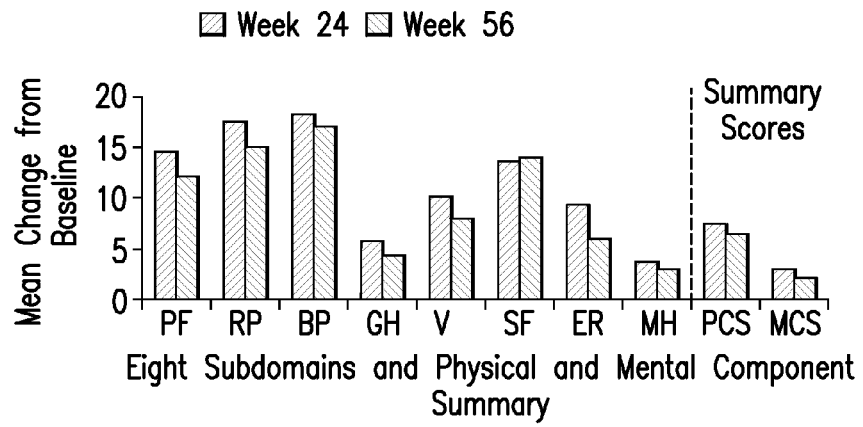

Physical Functioning (PF), Role Physical (RP), Bodily Pain (BP), General Health (GH), Vitality (V), Social Functioning (SF), Emotional Role (ER), Mental Health (MH), Physical Component Summary (PCS), and Mental Component Summary (MCS). Scale is from 0 to 100 with higher score indicating better quality of life.

FIG.12

HC/APAP CR = extended-release hydrocodone/acetaminophen;
Tab = tablet; qd = once daily; bid = twice daiily; wk = week
Scheduled study visits during the maintenance period took place
at wk 2 and every 4 wks from wk 4 through wk 56.

FIG.13

☆ Randomization on the morning following surgery only if, (1) pain intensity level was ≥ 40 mm on a visual analog scale (VAS, 100 mm, 0 = no pain and 100 = worst pain imaginable) and (2) pain intensity level was moderate or severe on categorical scale.

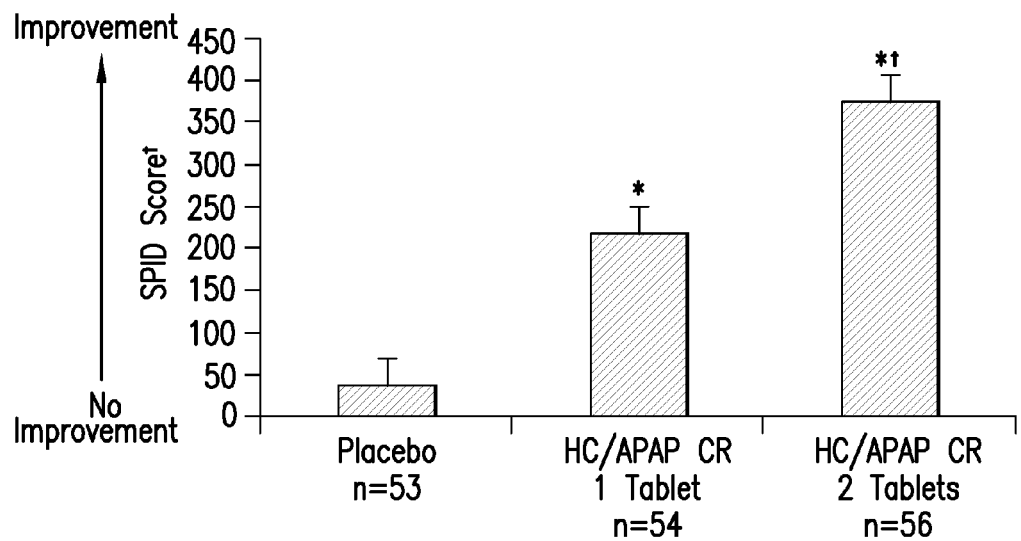

*P<.001 versus placebo, †P<.001 versus HC/APAP CR 1 tablet,
‡Time-interval weighted sum of pain intensity difference from baseline; higher scores indicate greater improvement in pain intensity from baseline.

FIG.16

| Washout | Titration<br>-1 wk- | Maintenance<br>-56 wks- | Taper<br>-1 wk- | Follow up<br>-1 wk- |
|---|---|---|---|---|
| | HC/APAP CR<br>1 Tab qd x 3d;<br>1 Tab bid x 4d | HC/APAP CR<br>2 Tabs bid | HC/APAP CR<br>1 Tab bid x 4d;<br>1 Tab qd x 3d | |
| Screening<br>Visit | Baseline | Wk<br>0 | Wk<br>56 | Wk<br>57 | Wk<br>58 |

HC/APAP CR = extended-release hydrocodone/acetaminophen;
Tab = tablet; qd = once daily; bid = twice daily; wk = week
Scheduled study visits during the maintenance period took place
at wk 2 and every 4 wks from wk 4 through wk 56.

FIG.17

EXTENDED RELEASE HYDROCODONE ACETAMINOPHEN AND RELATED METHODS AND USES THEREOF

CROSS REFERENCE

This claims priority to U.S. Provisional Patent Application No. 61/092,907, filed on Aug. 29, 2008, and U.S. Provisional Patent Application No. 61/028,053, filed on Feb. 12, 2008, the entire contents of all of which are fully incorporated herein by reference.

BACKGROUND

A patient's quality of life is adversely affected by pain. Further, this quality of life is associated with loss of work productivity, which impacts both the patient and its employer adversely.

Thus, for example, moderate to severe pain and physical disability that are symptoms of osteoarthritis (OA) may profoundly affect many aspects of patients' quality of life including the activities of daily living (ADLs). Moreover, in other pain conditions such as, low back pain (LBP), the total cost in loss of productivity in the U.S. exceeds $100 billion/year. Among active U.S. workers, pain conditions such as LBP, cost employers approximately $61.2 billion/year in lost productive time.

Generally, pain is treated with NSAIDs or combination opioids to provide effective analgesia in patients with moderate to severe chronic osteoarthritis (OA) pain when less potent treatments are not effective or tolerable, or are contraindicated. Currently, combination opioids are available only in immediate-release formulations. These combinations however may not adequately address several quality of life concerns. Therefore, improvement in quality of life is desirable through new formulations, which also reduce loss of productivity, thereby positively impacting both the patient and its employers.

BRIEF SUMMARY OF PREFERRED EMBODIMENTS

The present invention generally provides a method of treatment and improvement of quality of life for patients adversely affected by various pain conditions. One preferred embodiment provides a method of treatment of acute pain, moderate to moderately severe pain, chronic pain, non-cancer pain, osteoarthritic pain, bunionectomy pain or lower back pain in a patient in need thereof, comprising providing at least one or two dosage form having about 15 mg of hydrocodone and its salt and about 500 mg of acetaminophen, once, twice or thrice daily. Preferably, the dosage form is about 30 mg of hydrocodone and about 1000 mg of acetaminophen taken twice daily. Alternatively, the dosage form is about 15 mg of hydrocodone and about 500 mg of acetaminophen taken twice daily. Also, preferably, these dosage forms may be taken by the patient with or without food. In another aspect of the invention, co-administration of about 240 ml of 40%, 20%, 4% and 0% ethanol on the single dosage form affects the mean maximum plasma concentration level Cmax by ≤25% for both hydrocodone and acetaminophen in the patient. In another aspect, the Cmax and the AUC of hydrocodone for a patient with mild to moderately impaired hepatic function is substantially similar to the normal patient and the Cmax and the AUC of acetaminophen for a patient with mildly impaired hepatic function is substantially similar to the normal patient. Also, no overall statistical differences in effectiveness is observed for the patient metabolizing hydrocodone when the patient is a poor or competent metabolizer of Cytochrome P450 2D6 polymorphism.

Another embodiment of the invention provides a method of improving quality of life in a patient in need thereof, comprising administering to said patient a controlled release twice daily dosage form including acetaminophen and hydrocodone or a therapeutically effective salt thereof. In yet another embodiment, the invention provides a method of reducing loss of productivity in a patient having pain related condition, comprising administering to said patient a controlled release twice daily dosage form including acetaminophen and hydrocodone or a therapeutically effective salt thereof. Preferably, the dosage form comprises about 15 mg of hydrocodone or a therapeutically acceptable salt thereof and about 500 mg of acetaminophen. Or preferably, in all above embodiments, the dosage form comprises about 15 mg of hydrocodone or a therapeutically acceptable salt thereof and about 500 mg of acetaminophen. Alternatively, the dosage form comprises about 30 mg of hydrocodone or a therapeutically acceptable salt thereof and about 1000 mg of acetaminophen.

These and other objects will be highlight throughout the detailed description of the preferred embodiments. The summary must not be deemed to limit the scope of the invention.

BRIEF SUMMARY OF FIGURES

FIG. 2 provides mean Hydrocodone and Acetaminophen Plasma Concentration Over 12 Hours Following Single Dose of 1, 2 and 3 Tablet(s) Vicodin CR (Hydrocodone Bitartrate 15 mg/Acetaminophen 500 mg)

FIG. 8 provides the study design for Example VII.

FIG. 9 provides work productivity and activity impairment (efficacy evaluable dataset).

FIG. 10 provides the study design for Example VIII.

FIG. 12 provides SF-36 health status survey results (efficacy evaluable dataset).

FIG. 13 provides the study design for Example IX.

FIG. 16 provides SPID score (VAS), for 0-12 hours.

FIG. 15 provides the study design for Example XVI.

DETAILED DESCRIPTION OF PREFERRED EMBODIMENTS

Figure 1:
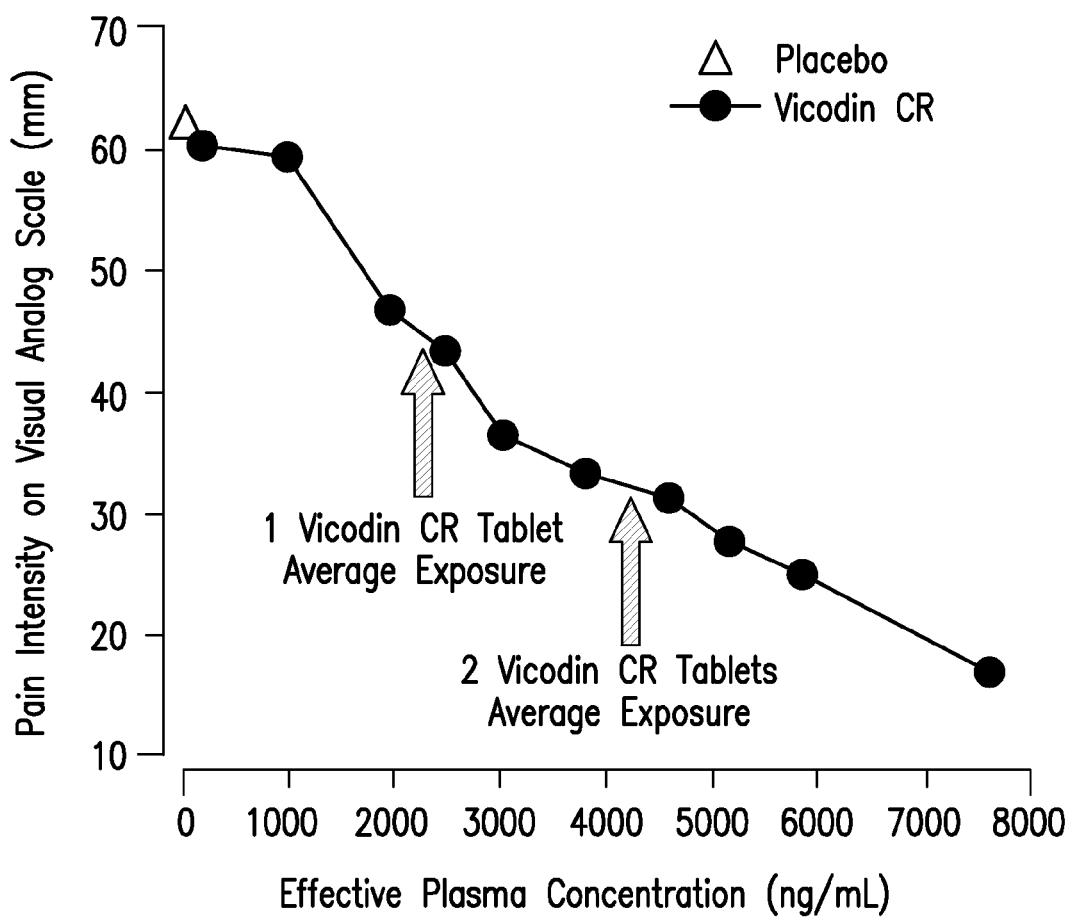
FIG. 1 provides exposure-Response Relationships of Vicodin CR in Acute Pain.

Vicodin CR is indicated for the relief of moderate to moderately severe pain. It is administered orally and may be taken with or without food. Vicodin CR should be swallowed whole, and must not be chewed, divided, crushed, or dissolved. The recommended adult dosage is two tablets twice daily (approximately every 12 hours), not to exceed 4 tablets in 24 hours. As with other opioid drug products, it is critical to initiate the dosing regimen for each patient individually, taking into account the patient's prior opioid and non-opioid analgesic treatment. Attention should be given to:

1. the general condition and medical status of the patient;
2. the daily dose, potency, and kind of analgesic(s) the patient has been taking;
3. the patient's opioid exposure and opioid tolerance (if any); and
4. the balance between pain control and adverse experiences.

Care should be taken to use low initial doses of Vicodin CR in patients who are not already opioid-tolerant, especially those who are receiving concurrent treatment with muscle relaxants, sedatives, or other CNS active medications. The tolerability of Vicodin CR may be improved by initiating therapy with one tablet once or twice daily before increasing to two tablets twice daily.

Patients with acute pain may be started on two tablets twice daily if necessary. The maximum dose of Vicodin CR evaluated in controlled studies was 2 tablets twice daily. It is recommended that patients who do not obtain satisfactory pain relief with two tablets twice daily be re-evaluated.

In treating pain, it is vital to assess the patient regularly and systematically. Therapy should also be regularly reviewed and adjusted based upon the patient's own reports of pain and side effects and the health professional's clinical judgment. When the patient no longer requires therapy with Vicodin CR, doses should be tapered gradually to prevent signs and symptoms of withdrawal in the physically dependent patient.

Vicodin CR contains 15 mg hydrocodone bitartrate and 500 mg acetaminophen. Vicodin CR contains hydrocodone, an opioid with an abuse liability and is a Schedule III controlled substance. Vicodin CR and other opioids used in analgesia, have the potential for being abused and are sought by drug abusers and people with addiction disorders and are subject to criminal diversion.

Chronic Pain Studies

Two double-blind, placebo-controlled, 17-week clinical studies were conducted; one study in patients with chronic low back pain (CLBP) and one study in patients with osteoarthritis (OA) pain. In the CLBP study, patients were enrolled in a 3-week Open-Label Titration Period (where all patients titrated up to Vicodin CR 2 tablets twice daily), which was then followed by a randomized 12-week Double-Blinded Treatment period where patients received either Vicodin CR 1 tablet twice daily, Vicodin CR 2 tablets twice daily, or placebo. In the OA study, patients were randomized to either Vicodin CR 2 tablets twice daily or placebo, initially, into a three-week Titration Period; which was then followed by the 12-week Maintenance Period. Both studies had a one-week Taper Period along with a one-week Follow-up Period for a total duration of 17 weeks. Treatment emergent adverse reactions reported ≥5% of patients during the CLBP and OA studies are presented in Tables 1 and 2 below. Adverse reactions which occurred at a rate less than or equal to placebo, are not included in the tables below in this section.

TABLE 1

Treatment-Emergent Adverse Reactions Reported in ≥5% of Patients During the Open-Label Titration Period and Double-Blind Treatment Period (17-Week Study in Patients with Chronic Low Back Pain)

| Adverse Reaction (Preferred Term) | Open-label Titration (Up to 3 Weeks dosing) All Enrolled (N = 770) | Double-Blind Treatment Period (12 Week Dosing) | | |
|---|---|---|---|---|
| | | VICODIN CR 1 Tablet (N = 170) | VICODIN CR 2 Tablet (N = 169) | Placebo (N = 172) |
| Constipation | 29% | 4% | 7% | 2% |
| Nausea | 26% | 5% | 9% | 3% |
| Somnolence | 14% | 4% | 2% | 0% |
| Pruritus | 10% | 1% | 0% | <1% |
| Headache | 9% | 5% | 4% | 6% |
| Dizziness | 8% | 1% | 2% | 1% |
| Vomiting | 8% | 3% | 4% | 1% |
| Fatigue | 6% | 0% | 2% | <1% |
| Diarrhea | 2% | 4% | 5% | 3% |

TABLE 2

Treatment-Emergent Adverse Reactions Reported in ≥5% of Patients During the Double-Blind Treatment Period (17-Week Study in Patients with Osteoarthritis)

| | Double-Blind Treatment Period (17-Week Study) | |
|---|---|---|
| Adverse Reaction (Preferred Term) | VICODIN CR 2 Tablet (N = 430) | Placebo (N = 443) |
| Constipation | 44% | 14% |
| Nausea | 29% | 10% |
| Somnolence | 13% | 4% |
| Pruritus | 10% | 4% |
| Dizziness | 10% | 3% |
| Vomiting | 8% | <1% |
| Fatigue | 6% | 3% |
| Insomnia | 6% | 3% |
| Arthralgia | 5% | 4% |
| Diarrhea | 5% | 4% |
| Pain in Extremity | 5% | 4% |

Acute Pain Study

In a double-blind, placebo-controlled acute pain study of post unilateral, first metatarsal bunionectomy surgery, patients were randomized to receive either Vicodin CR 1 tablet twice daily, Vicodin CR 2 tablets twice daily or placebo for 2 days (total of 4 doses). Treatment-emergent adverse reactions reported in ≥5% of patients during the acute bunionectomy study are presented in Table 3.

TABLE 3

Treatment-Emergent Adverse Reactions Reported in ≥5% of Patients During the Acute Bunionectomy Study

| | Double Blind Treatment Period (2 Days Dosing) | | |
|---|---|---|---|
| Adverse Reaction (Preferred Term) | VICODIN CR 1 Tablet (N = 54) | VICODIN CR 2 Tablet (N = 56) | Placebo (N = 53) |
| Nausea | 46% | 70% | 13% |
| Vomiting | 19% | 39% | 6% |
| Somnolence | 19% | 30% | 11% |
| Headache | 24% | 29% | 17% |
| Dizziness | 26% | 23% | 0% |
| Pruritus | 11% | 16% | 0% |
| Anorexia | 6% | 0% | 0% |
| Constipation | 9% | 9% | 4% |
| Diarrhea | 2% | 5% | 0% |
| Pruritus Generalized | 0% | 5% | 0% |
| Rash | 0% | 5% | 2% |

Open-Label Safety Study

In an Open-Label Safety Study, patients with osteoarthritis or chronic low back pain received Vicodin CR 2 tablets twice daily for up to 13 months. Adverse events reported in this Open-Label Study were similar to those observed in the controlled trials in acute and chronic pain. The adverse events reported in ≥5% of patients during this Open-Label Safety Study, regardless of investigator assessment of causality, are included in Table 4.

TABLE 4

Summary of Treatment-Emergent Adverse Events Occurring in ≥5% of Patients During 13-Month Open-Label Safety Study

| Adverse Event (Preferred Term) | VICODIN CR 2 Tablet (N = 431) |
|---|---|
| Constipation | 32% |
| Nausea | 26% |
| Headache | 18% |
| Somnolence | 12% |
| Pruritus | 9% |
| Nasopharyngitis | 7% |
| Upper Respiratory Tract Infection | 7% |
| Dizziness | 7% |
| Vomiting | 7% |
| Diarrhea | 6% |
| Insomnia | 6% |
| Fatigue | 6% |
| Back Pain | 6% |
| Anxiety | 5% |
| Depression | 5% |
| Influenza | 5% |

Adverse Reactions Reported in All Clinical Trials

A total of 1968 patients were treated with Vicodin CR in the controlled and open-label clinical trials. The clinical trials consisted of patients with moderate to severe chronic low back pain, osteoarthritis or post surgical pain. The adverse reactions reported by (≥1 to <5%) patients treated with Vicodin CR in the clinical trials organized by MedDRA's (Medical Dictionary for Regulatory Activities) System Organ Class not listed above were:

Gastrointestinal Disorders
  Abdominal pain, abdominal pain upper, dry mouth, dyspepsia, toothache
General Disorders and Administration Site Conditions
  Asthenia, edema peripheral, pain, pyrexia
Infections and Infestations
  Gastroenteritis, gastroenteritis viral, sinusitis, urinary tract infection
Injury, Poisoning and Procedural Complications
  Fall
Musculoskeletal and Connective Tissue Disorders
  Muscle spasms, myalgia
Nervous System Disorders
  Lethargy, sedation
Respiratory, Thoracic and Mediastinal Disorders
  Cough, pharyngolaryngeal pain
Skin and Subcutaneous Tissue Disorders
  Hyperhidrosis
Vascular Disorders
  Flushing, hot flush, hypertension Other less common adverse reactions that were seen in <1% of the Vicodin CR trials not listed above include the following in alphabetical order (like terms were combined as appropriate): Adjustment disorder, affect lability, agitation, amnesia, anemia, angina pectoris, arthritis, asthma, atrial fibrillation, bladder disorder, blindness, blood alkaline phosphatase increased, blood/electrolyte abnormal, blood glucose increased, blood in stool, blood testosterone and estrogen decreased, bruxism, cardiac arrest, cardiac failure congestive, cerebrovascular accident, cholecystitis, confusional state, deep vein thrombosis, dehydration, depressed level of consciousness, dermatitis, diverticulitis, drug eruption, drug intolerance, drug withdrawal syndrome, dry eye, dysarthria, dysgeusia, dysphagia, dysphonia, dyspnea, energy increased, enuresis, epididymitis, epistaxis, erectile dysfunction, erythema, euphoric mood, feeling abnormal, feeling drunk, feeling of body temperature change, feeling of relaxation, gait disturbance, gastric ulcer, hemorrhage, gastritis, gastrointestinal disorder, hematoma, hemoptysis, hemorrhoids, hallucination, hearing impaired, heart rate increased, hepatic enzyme increased, hiccups, hypoesthesia, hypoglycemia, hypotension including orthostatic hypotension, hypoxia, increased appetite, infection, injury, logorrhea, menstrual disorder, mental impairment, motor dysfunction, muscle twitching, muscular weakness, myocardial infarction, myositis, neoplasm malignant, nephrolithiasis, neuropathy, nightmare, palpitations, pancreatitis, paraesthesia, paranoia, peripheral vascular disorder, photophobia, piloerection, prostatic disorder, pulmonary embolism, rectal fissure, renal failure, respiratory rate decreased, restless legs syndrome, rhinorrhea, seasonal allergy, sexual dysfunction, sleep apnea syndrome, sleep disorder, substance abuse, suicide attempt, syncope, thrombocytopenia, tinnitus, transitory deafness, tremor, urinary retention, urine analysis abnormal, urticaria, vision blurred, weight fluctuation.

Adverse Events with Immediate-Release Vicodin

In addition to those mentioned above, the following adverse experiences have been reported in patients receiving immediate-release Vicodin but were not observed in clinical trials with Vicodin CR.

Blood and Lymphatic Disorders
Agranulocytosis, thrombocytopenia
Ear and Labyrinth Disorders
Hearing impairment or permanent loss, predominantly in patients with chronic overdose.

Ethanol Interaction

In in vitro studies of ethanol effects on Vicodin CR, the release of hydrocodone and acetaminophen was not modified in the presence of ethanol (0% and 40% ethanol) within the first 3 hours but showed slight elevations in amounts released at 5 to 7 hours. No dose dumping of hydrocodone was shown in vitro within the first 2 hours in the dissolution media (0.01N HCl and Simulated Gastric Fluid) containing 4%, 20%, and 40% ethanol. An in vivo study examined the effect of co-administration of 240 mL of 40%, 20%, 4% and 0% ethanol on the bioavailability of a single tablet of Vicodin CR, in healthy, fasted subjects. No dose dumping was observed for Vicodin CR when co-administered with ethanol. Hydrocodone and acetaminophen mean maximum plasma concentration ($C_{max}$) increased by ≤25% when Vicodin CR was co-administered with up to 40% ethanol. The area under the plasma concentration-time curves (AUC) for hydrocodone and acetaminophen administered with different ethanol concentrations were equivalent to that of Vicodin CR alone (i.e., co-administration with 0% ethanol). The variability in hydrocodone and acetaminophen exposures ($C_{max}$ and AUC) was not affected by ethanol coadministration. There was no relationship between changes in $C_{max}$ and observed clinical pharmacodynamic changes (pupillometry, Ramsey Sedation Scale).

Hepatic Impairment

The effects of hepatic insufficiency on the pharmacokinetics of Vicodin CR were studied in 24 subjects: 8 subjects with normal hepatic function, 8 subjects with mild (Child-Pugh Classification A) stable chronic hepatic impairment and 8 subjects with moderate (Child-Pugh Classification B) stable chronic hepatic impairment. Following oral administration of a single tablet of Vicodin CR, mean $C_{max}$ and AUC values of hydrocodone were similar in normal subjects and subjects with mild and moderate hepatic impairment. Mean $C_{max}$ and AUC values of acetaminophen were similar in normal subjects and subjects with mild hepatic impairment, and 34 to 42% higher in subjects with moderate hepatic impairment.

Gender

There were no differences in hydrocodone and acetaminophen pharmacokinetics, or clinically meaningful differences in efficacy results or incidence of adverse reactions between men and women in clinical studies with Vicodin CR.

Cytochrome P450 2D6 Poor Metabolizers

CYP2D6 polymorphism had no statistically significant impact on hydrocodone pharmacokinetics. Seven percent of genotyped patients receiving Vicodin CR in an acute bunionectomy study (6/90) and a chronic osteoarthritis study (21/300) were poor metabolizers. No overall differences in effectiveness were observed between poor and competent metabolizers of cytochrome P450 2D6.

Vicodin CR is an orally administered, extended-release tablet. Each extended release tablet contains 15 mg of hydrocodone bitartrate and 500 mg of acetaminophen. After the release of the nominal drug load, a tablet shell is eliminated in the stool. Hydrocodone bitartrate hemipentahydrate is an opioid analgesic and antitussive and occurs as fine, white crystals or as a crystalline powder. It is affected by light. The chemical name is: 4,5α-epoxy-3-methoxy-17-methylmorphinan-6-one tartrate (1:1) hydrate (2:5). The molecular formula is $C_{18}H_{21}NO_3 \cdot C_4H_6O_6 \cdot 2\frac{1}{2}H_2O$ and the molecular weight is 494.50. The chemical structure of hydrocodone bitartrate is:

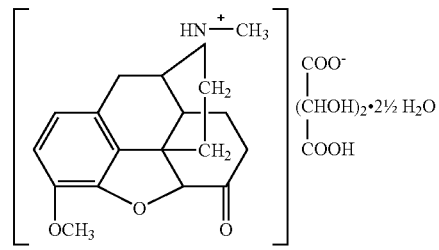

Acetaminophen, 4'-hydroxyacetanilide, a slightly bitter, white, odorless, crystalline powder, is a non-opiate, non-salicylate analgesic and antipyretic. The molecular formula is $C_8H_9NO_2$ and the molecular weight is 151.16. The chemical structure of acetaminophen is:

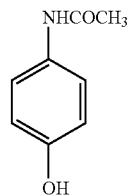

In addition each tablet contains the following inactive ingredients: stearic acid, croscarmellose sodium, copovidone, poloxamer 188, hydroxyethyl cellulose, ferric oxide (red), hydroxypropyl cellulose, polyethylene oxide, carnauba wax, acetone, butylated hydroxytoluene (BHT), Opadry (White), hydroxypropyl methylcellulose 2910, cellulose acetate, polyethylene glycol 3350, povidone, purified water, magnesium stearate, colloidal silicon dioxide, and sodium chloride.

Clinical Pharmacology

Mechanism of Action

Hydrocodone is a semisynthetic opioid analgesic and antitussive with multiple actions qualitatively similar to those of other opioid mu receptor agonists. Most of these involve the central nervous system and smooth muscle. The precise mechanism of action of hydrocodone and other opiates is not known, although it is believed to relate to the existence of opiate receptors in the central nervous system. The analgesic action of acetaminophen involves peripheral influences, but the specific mechanism is as yet undetermined. Antipyretic activity is mediated through hypothalamic heat regulating centers. Acetaminophen inhibits prostaglandin synthetase. Therapeutic doses of acetaminophen have negligible effects on the cardiovascular or respiratory systems; however, toxic doses may cause circulatory failure and rapid, shallow breathing.

Pharmacodynamics

Exposure-response relationship was determined from three randomized, double-blind, placebo-controlled acute pain studies in over 450 patients receiving either Vicodin CR 1 tablet, Vicodin CR 2 tablets, immediate-release tablet (hydrocodone bitartrate 10 mg/acetaminophen 325 mg) or placebo. A direct linear relationship was found between the combined hydrocodone and acetaminophen exposure (concentration in plasma) and clinical response (pain intensity on visual analog scale) after accounting for the time course of placebo response (FIG. 1).

The continuous exposure-response relationship between the effective plasma concentration (combined acetaminophen and potency-adjusted hydrocodone plasma concentrations) and the clinical response indicates a proportional dose-response between one and two tablets of VICODIN CR. The estimated difference in pain intensity on visual analog scale, after accounting for the time course of placebo response, is approximately 14 mm and 30 mm for one tablet and two tablets of Vicodin CR, respectively.

Pharmacokinetics

Absorption:

Following oral administration of Vicodin CR in healthy subjects, the $C_{max}$ for hydrocodone was achieved between 4 to 7 hours. Mean plasma acetaminophen concentrations increase rapidly and reach maximum at about 1 hour. $C_{max}$ and AUC for both hydrocodone and acetaminophen were proportional to dose after single dose administration of 1, 2 and 3 tablets (FIG. 2).

Figure 3:
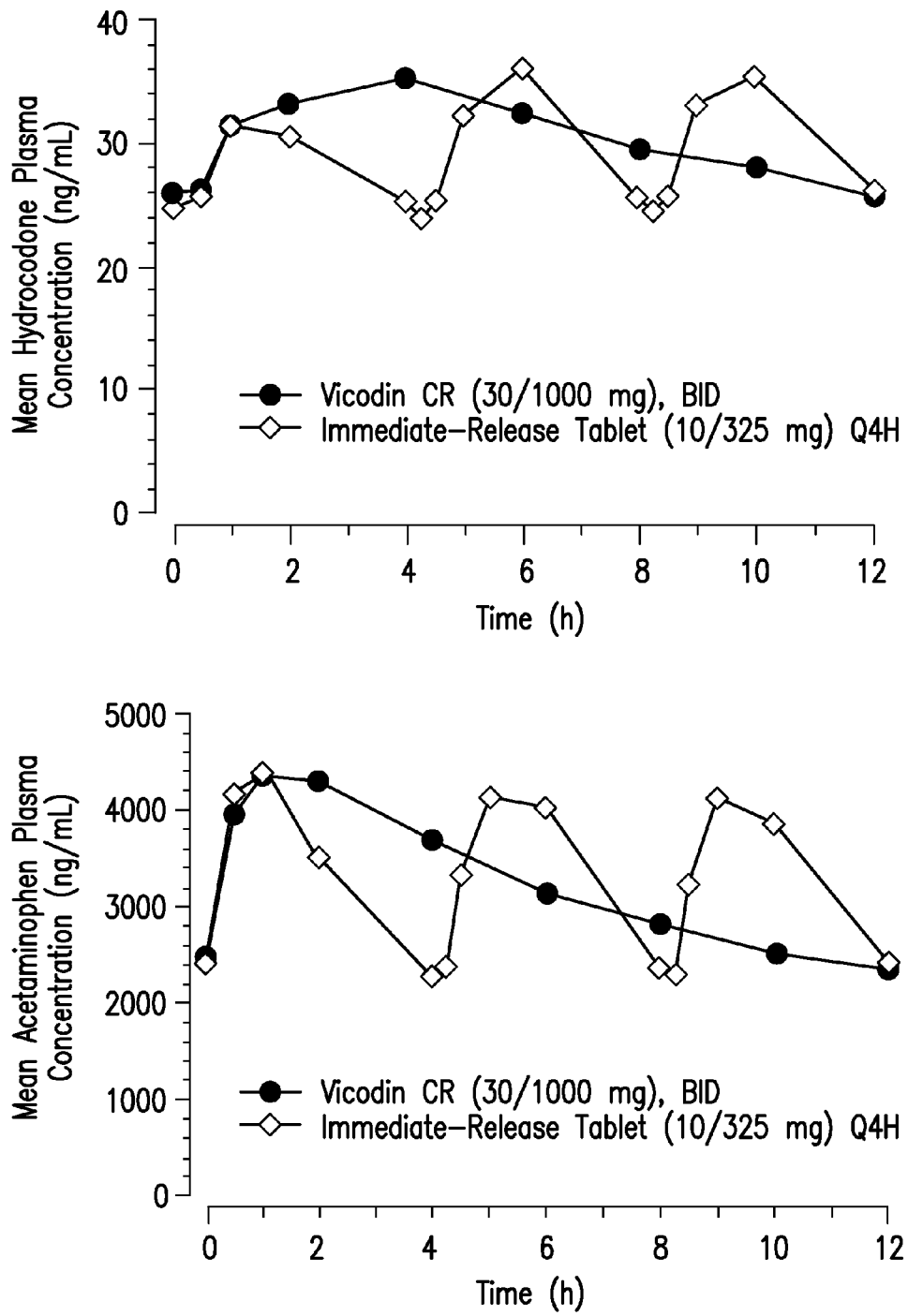
FIG. 3 provides mean Steady-State Hydrocodone and Acetaminophen Plasma Concentration After Administration of 2 Tablets Vicodin CR (Hydrocodone Bitartrate 15 mg/Acetaminophen 500 mg) Twice Daily and 1 Immediate-Release Tablet (Hydrocodone Bitartrate 10 mg/Acetaminophen 325 mg) Every 4 Hours.

Steady state for hydrocodone and acetaminophen concentrations was achieved by 24 hours with minimal accumulation when Vicodin CR was administered every 12 hours. There was less fluctuation between peak and trough plasma concentrations for the Vicodin CR than for the immediate-release tablet (hydrocodone bitartrate 10 mg/acetaminophen 325 mg) every four hours (FIG. 3).

Effect of Food:

Vicodin CR may be taken with or without food, as food has no effect on $C_{max}$ or AUC of hydrocodone and acetaminophen.

Distribution:

Hydrocodone is structurally similar to other opioid analgesics (hydromorphone and oxycodone). It is not anticipated, therefore, that hydrocodone would be extensively bound to plasma proteins. Following administration of Vicodin CR, the apparent volume of distribution for hydrocodone ranged from 277 to 714 L in healthy subjects and patients with moderate to severe pain. Acetaminophen has been reported to be 15-21% bound at higher drug concentrations that have been associated with overdosage (280 μg/mL). Following administration of Vicodin CR, the apparent volume of distribution for acetaminophen ranged from 78 to 245 L in healthy subjects with moderate to severe pain.

Metabolism:

Hydrocodone exhibits a complex pattern of metabolism including N-demethylation (norhydrocodone), O-demethylation (hydromorphone) and 6-keto reductions to the corresponding 6-(alpha) and 6-(beta)-hydroxy metabolites. Acetaminophen is principally metabolized by the liver (conjugation).

Clinical Studies

The efficacy and safety of Vicodin CR tablets have been evaluated in both acute and chronic pain. A total of 1968 patients received Vicodin CR in studies of chronic low back pain, non-cancer pain, osteoarthritis pain or post surgical (bunionectomy) pain and a long-term open-label safety study.

Seventeen (17)-Week Study in Patients with Chronic Low Back Pain

Patients with a diagnosis of chronic low back pain (CLBP) (for at least 6 months duration) who were suboptimally responsive to their current therapy entered a three-week Open-Label Dose Titration Period (dose increased to 2 tablets twice daily). Most enrolled patients were Caucasian (86%) and the majority of the patients were female (59%). Mean age was 49.2 years, with a range from 21 to 76 years. Of the patients who completed the Open-Label Period, the mean±SD VAS (0-100; with 0 mm=no pain and 100 mm=worst pain imaginable) score at Screening was 77.0±13.9 and at Baseline (beginning of the Double-Blind Period) was 25.1±14.8 Vicodin CR 2 tablet, 24.4±13.1 Vicodin CR 1 tablet and 24.3±15.2 placebo treatment groups respectively. Sixty-six percent of the patients enrolled were able to titrate to a tolerable dose and were randomized into a 12-week Double-Blind Maintenance Period with Vicodin CR 2 tablet, 1 tablet or placebo. During the first 7 days of the Double-Blind Maintenance Period placebo treated patients were gradually tapered off their dose of Vicodin CR in order to minimize opioid withdrawal symptoms in the placebo subjects. Of the 511 randomized patients, 169 were randomized to Vicodin CR 2 tablet twice daily, 170 to Vicodin CR 1 tablet twice daily and 172 to placebo. Seventy-one percent of the Vicodin CR treated subjects completed the 12-week treatment period compared to fifty-two percent of the placebo treated subjects.

Figure 4:
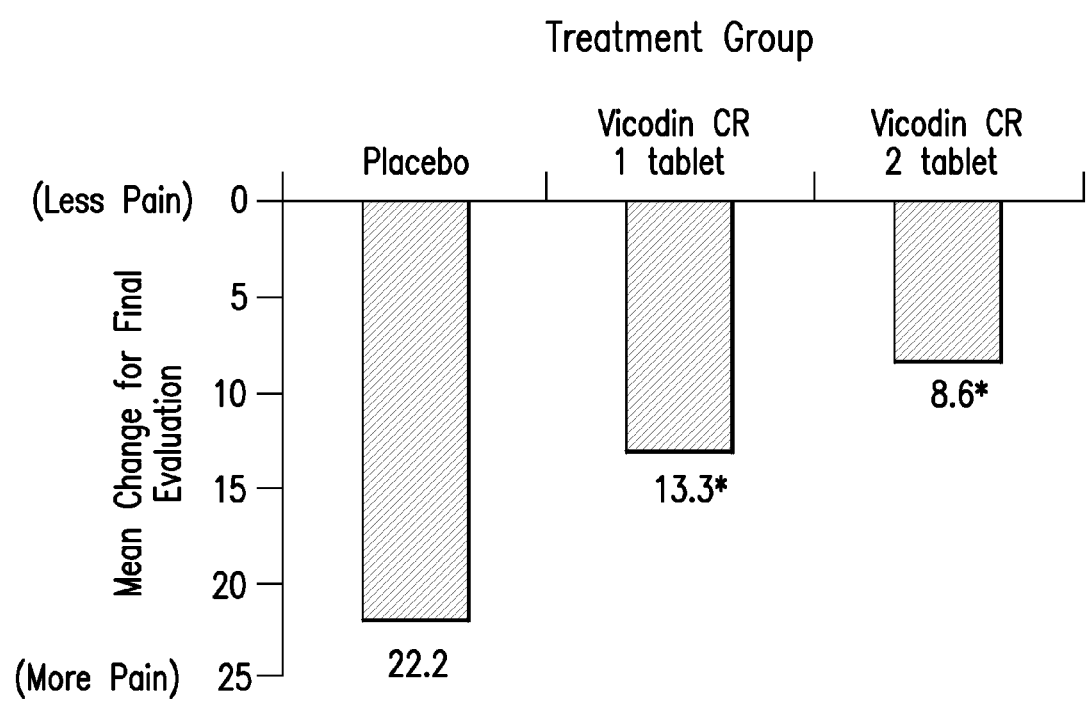
FIG. 4 provides mean Change in Subject's Assessment of CLBP Intensity VAS Scores from Double-Blind Baseline to Final Evaluation in CLBP Study (Double-Blind Maintenance Period; Efficacy Evaluable Data Set)*Statistically significant (p≤0.05) difference versus placebo using an ANCOVA model with factors for treatment and study center with Double-Blind Baseline VAS pain intensity score as a covariate.

The primary efficacy analysis for the Double-Blind Maintenance Period was the assessment of the mean change in Subject's Assessment of CLBP Intensity by VAS from Double-Blind Baseline to Final evaluation. A significantly smaller increase in pain scores was observed in the Vicodin CR 2 tablet treatment group as compared to the placebo treatment group as shown in FIG. 4.

Figure 5:
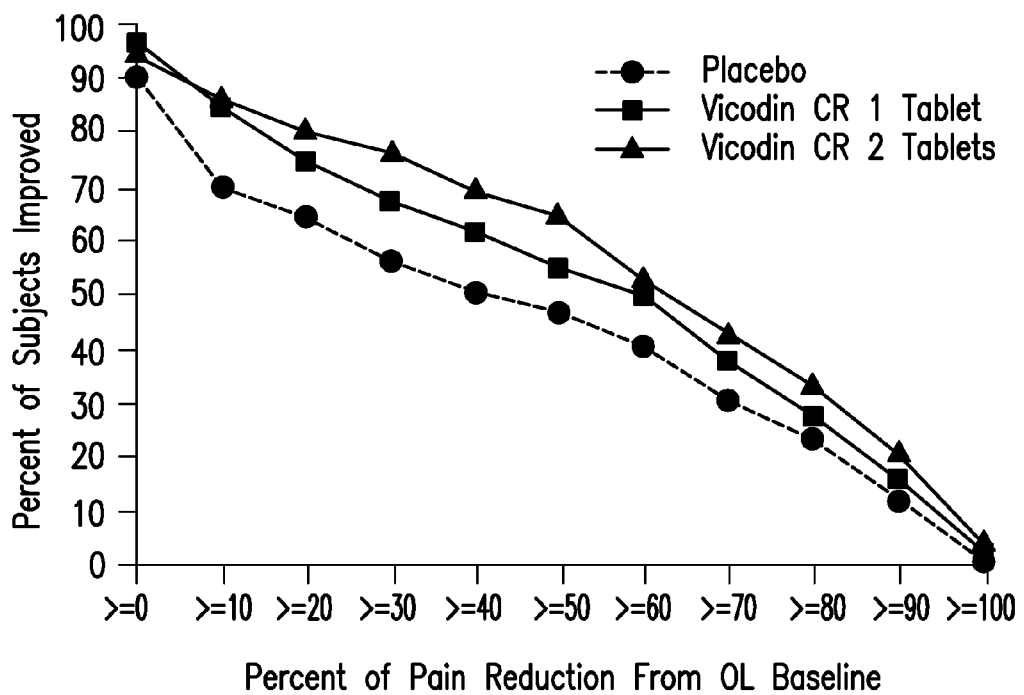
FIG. 5 provides proportion of Patients Achieving Various Levels of Pain Reduction from Open-Label Baseline to the Final Evaluation for Patient's Assessment of CLBP Intensity VAS (DB Maintenance Period Efficacy Evaluable Data Set). Note: P-value=0.001 for Vicodin CR 2 tablet vs. placebo and p-value=0.049 for Vicodin CR 1 tablet vs. placebo for test of difference in the distribution between treatment groups using Monte Carlo exact Kolmogorov-Smimov test.
Figure 6:
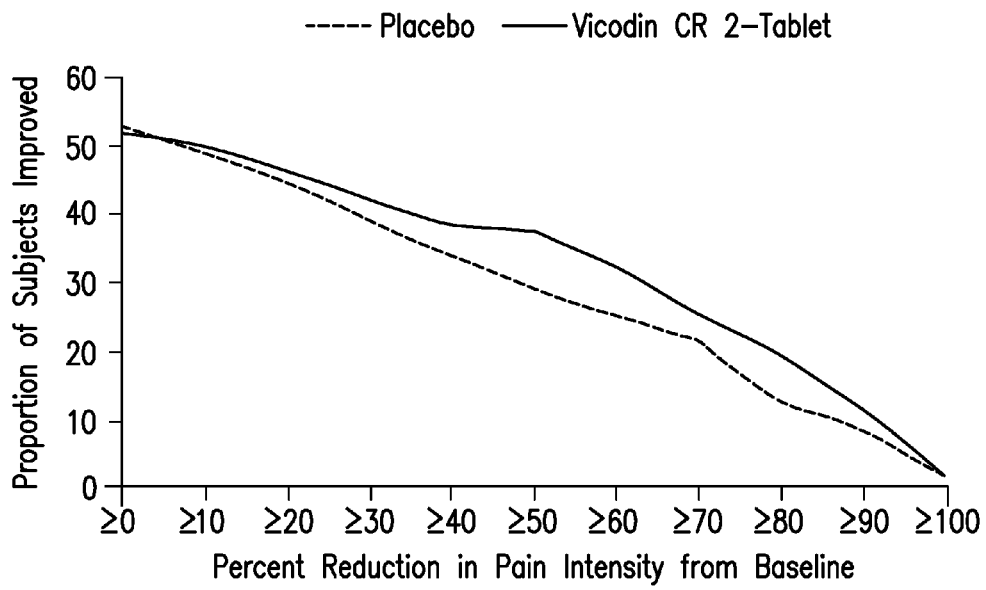
FIG. 6 provides proportion of Subjects Achieving Various Levels of Pain Reduction From Baseline to the Maintenance Week 12 Visit for Subject's Assessment of Arthritis Pain Intensity by VAS in Chronic OA Pain Study. Note: The p-value=0.055 for test of difference in the distribution between treatment groups using Monte Carlo exact Kolmogorov-Smimov test.

The proportion of patients with various levels of pain reduction from baseline to study endpoint is shown in FIG. 5.

Seventeen (17)-Week Study in Patients with Osteoarthritis

Eight hundred and seventy-three patients with osteoarthritis (OA) of the hip or knee were randomized to either Vicodin CR 2 tablets twice daily or placebo in a double-blind, placebo controlled study. The study was comprised of a Double-Blind 3-week Titration Period, followed by a 12-week Maintenance Period, one-week Taper period and a one-week Follow-up Period. There were 440 patients randomized to Vicodin CR and 433 randomized to placebo; 489 completed the study (238 Vicodin CR and 251 placebo patients). Most patients were Caucasian (84%) and the majority of the patients were female (64%). Mean age was 58.6 years, with a range from 23 to 80 years.

Treatment with Vicodin CR 2 tablet twice daily resulted in an improvement in the mean Subject's Assessment of Arthritis Pain Intensity scores from Baseline to Maintenance Week 12 as compared to placebo (p=0.055) and significantly increased the proportion of patients with at least a 50% reduction in pain score from Baseline (37% Vicodin CR vs 29% placebo). For various degrees of improvement from Baseline to study endpoint (Maintenance Week 12), FIG. 5 shows the proportion of patients achieving that degree of improvement. The figure is cumulative, so that patients whose change from Baseline is, for example, 50%, are also included at every level of improvement below 50%. Patients who did not complete the study were assigned 0% improvement.

Acute Bunionectomy Study

Figure 7:
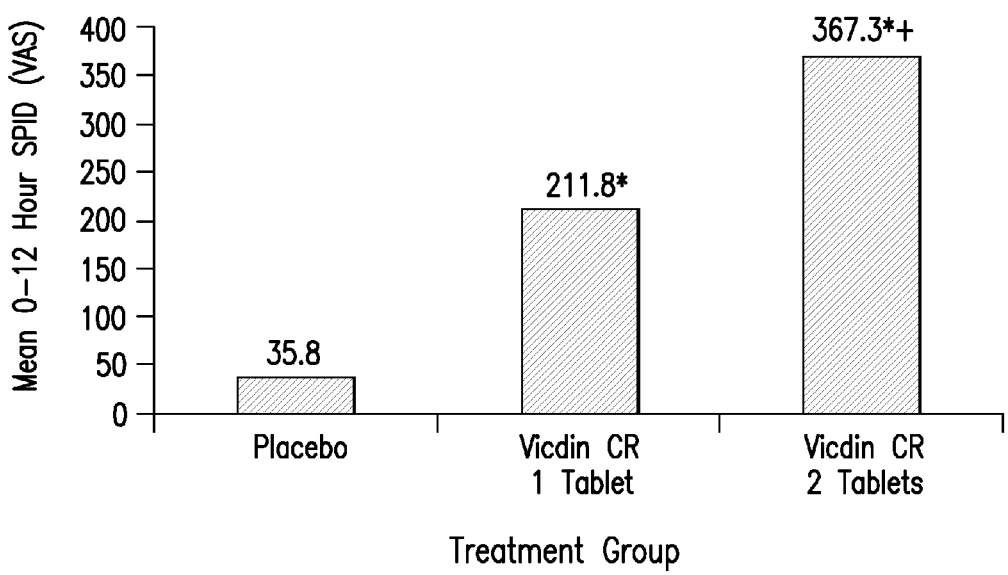
FIG. 7 provides total Pain Reduction Over 12 Hours; Mean SPID VAS (0-12 Hours) Scores Following the Initial Study Drug Dose Using LOCF in Acute Pain Study (ITT Data Set). *Statistically significant (p≤0.05) difference versus placebo, using an ANCOVA model with factors for treatment, study center, and the Baseline VAS pain intensity score as a covariate. †Statistically significant (p≤0.05) difference versus Vicodin CR 1 tablet, using an ANCOVA model with factors for treatment, study center, and the Baseline VAS pain intensity score as a covariate.

In a double-blind, placebo controlled, multi-center, randomized two day study in patients status post primary, unilateral, first metatarsal bunionectomy surgery, 163 patients received either one or two tablets of Vicodin CR or placebo twice daily. Of the 163 patients enrolled, 110 were randomized to Vicodin CR and 53 were randomized to placebo; 159 patients completed the study (106 Vicodin CR and 53 placebo patients). Most patients were Caucasian (80%) and the majority of the patients were female (89%). Mean age was 42.1 years, with a range from 21 to 65 years. For the primary efficacy endpoint, there was a statistically significant reduction in pain intensity with Vicodin CR 2 tablets twice daily compared to placebo over the first twelve hour period postdose (Sum of Pain Intensity Differences [SPID])(see FIG. 7). Onset of pain relief occurred within one hour in patients taking Vicodin CR 2 tablets.

Open-Label Safety Study

In an open-label, multi-center, safety study, patients with either osteoarthritis or chronic low back pain received Vicodin CR 2 tablets for up to 13 months. There were 431 patients who were treated in the study; 191 (44%) completed one year and 242 (56%) completed 6 months of treatment. There were 246 patients (57%) who prematurely discontinued the study, including 112 (26%) withdrawals due to adverse events and 32 (7%) due to lack of efficacy.

As described above, a patient's quality of life is frequently adversely affected by pain. Further, this quality of life is associated with loss of work productivity, which impacts both the patient and its employer adversely. The present invention provides methods of improving quality of life and related conditions through safe and effective twice-daily, extended-release hydrocodone/acetaminophen (HC/APAP CR) formulation. Such formulations are described in U.S. patent application Ser. No. 10/949,141, (US 20050158382), Ser. No. 11/625,705 (US 20070190142), Ser. No. 11/780,625 (US 20090022798), Ser. No. 11/737,904 (US 20080031901) and Ser. No. 11/737,914 (US 20070281018), all of which are incorporated herein in its entirety by reference for all purposes. In certain embodiments, the formulation comprises a monoeximic pharmaceutical composition that comprises a single (namely, one) rate controlling mechanism that controls or modulates the rate of one or more drugs that are released from the dosage form. The following are considered to be examples of monoeximic drug delivery formulations: (1) a single rate controlling mechanism mixed with a drug and compressed such that the drug is slowly released upon exposure to one or more aqueous solutions (a "monoeximic matrix system"): and (2) (a) a core comprising (i) a drug mixture, the drug mixture comprising an excipient such that the mixture rapidly releases drug upon exposure to one or more aqueous solutions (such as in an aqueous environment), and (ii) an osmotically active mixture that swells in response to absorption of aqueous solutions, and (b) a single rate controlling mechanism surrounding the core with an orifice formed therein, wherein the membrane permits water or liquids to slowly flow into the core, which thereby causes the osmotically active mixture to swell, and which swelling causes the core to be exuded through the orifice into the fluids of the gastrointestinal tract of a human if the human swallows the monoeximic drug delivery composition (a "monoeximic osmotic system"). In most preferred embodiment, the formulation comprises about 15 mg hydrocodone bitartrate pentahemihydrate and about 500 mg of acetaminophen.

Following examples are provided to illustrate the preferred embodiments of the inventions, and should not be deemed to limit its scope. Thus, while treatment and improvements of quality of life for osteoarthritis and lower back pain are specifically provided, the invention should not be deemed to address only these pain conditions, however, should include other pain-related conditions known to one of skilled in the art. Moreover, these formulations specifically address moderate to severe pain conditions, however, one of ordinary skill in the art would appreciate, this formulation may be useful for treating other related conditions.

EXAMPLE I

Effects of 12-Hour Extended-Release Hydrocodone/Acetaminophen on Arthritis Status and Quality of Life in Patients with Osteoarthritis: A 12-Week Randomized Placebo-Controlled Study Methods: A randomized, multicenter, double-blind, placebo-controlled study was conducted in patients with moderate to severe chronic OA pain of the hip or knee (n=873). Patients received either 12-hour extended-release hydrocodone 15 mg/acetaminophen 500 mg (HC/APAP CR) 2 tablets or placebo twice daily. Primary efficacy results were reductions in pain intensity and are presented separately along with safety analyses and are not included in this presentation. Secondary efficacy measures included Subject's and Physician's Global Assessment (SGA and PGA) of Arthritis Status, the Western Ontario and McMasters University Osteoarthritis Index (WOMAC™), and the quality of life (SF-36v2™). These endpoints are reported here.

Results: At Week 12, statistically significantly greater improvements on WOMAC™ total score (p=0.001) and all three subscales [Pain, Stiffness, Physical Function (p=0.001 on all measures)] were observed with HC/APAP CR treatment. Similarly, at final evaluation, the physical component summary and the bodily pain sub-domain of the SF 36v2™ showed statistically significant improvements from baseline (p=0.044 and 0.004, respectively) with HC/APAP CR compared with placebo. In addition, statistically significantly greater benefits with HC/APAP CR were also observed on the SGA and PGA of arthritis status at Week 12 (p≤0.001).

Conclusions: HC/APAP CR treatment was associated with statistically significant improvements in both the disease-specific WOMAC™ instrument and the universal measure SF-36v2™. These results suggest that HC/APAP CR may not only provide effective analgesia, but also improvements in quality of life in patients with moderate-severe OA pain.

EXAMPLE II

A Randomized, Multicenter, Double-Blind Study Comparing the Analgesic Efficacy of Extended Release Hydrocodone/Acetaminophen Tablets to Placebo in Patients with Osteoarthritis Methods: A randomized, multicenter, double-blind, placebo-controlled study was conducted in 873 patients with moderate to severe chronic OA pain of the hip or knee. The study was divided into 4 periods: up to 4-week screening/washout, 3-week titration, 12-week maintenance, and 1-week study drug taper. 430 patients received extended-release HC 15 mg/APAP 500 mg twice daily and 443 patients received placebo twice daily. The primary efficacy variable was the percent change from baseline (just prior to start of 3-week titration) to Week 12 of maintenance (final planned assessment in the maintenance period) in patients' assessment of arthritis pain intensity (API) using a 100 mm visual analog scale. The following methods were used to impute missing data: baseline observation carried forward (BOCF), and a mixed imputation method utilizing both BOCF and last observation carried forward (LOCF). Safety measures, including adverse events, were also compared between the treatment groups.

Results: Compared with placebo, HC/APAP CR demonstrated numerical improvement (P=0.055) in API score using BOCF for missing data imputation. However, a mixed imputation of the primary endpoint (using BOCF for subjects that prematurely discontinued due to AE or who did not have any post-baseline assessments, and LOCF for patients who prematurely discontinued for any other reason), demonstrated that HC/APAP CR statistically significantly improved API compared with placebo (P=0.008). Adverse events that occurred in ≥5% of patients in the HC/APAP CR group and that occurred with significantly greater incidence as compared to placebo were: constipation, nausea, vomiting, dizziness, somnolence, insomnia and pruritus.

Conclusions: The twice-daily extended-release HC/APAP CR formulation was an efficacious treatment that was well-tolerated in patients with moderate to severe chronic OA pain.

EXAMPLE III

Long-Term Impact of Pain-Related Work Productivity Among Low Back Pain Patients Taking 12-Hour Extended-Released Hydrocodone/Acetaminophen Tablets Methods: As part of a larger clinical trial reported elsewhere, the Work Productivity and Activity Impairment (WPAI) instrument was administered at baseline and weeks 24 and 56 to measure reduced productivity and overall work impairment due to health. The economic impact of improved work productivity and overall work impairment due to health after HC/APAP CR treatment was calculated as the difference in cost (using the 2007 U.S. average weekly wage of $885) from baseline to weeks 24 and 56. Analyses were also conducted by gender and pain intensity (0-10 numeric rating scale, NRS).

Results: In LBP patients, impairment while working due to health decreased from baseline by 22% at week 24 and 18% at week 56. This translates to an average estimated cost-savings per employee of $4738 at week 24, and $8864 at week 56. Similarly, overall work impairment due to health decreased from baseline by 24% at week 24 and 17% at week 56. This translates into an average potential savings to employers of $4992 and $8233 at weeks 24 and 56. When the study population was stratified by gender, overall work impairment cost-savings to employers were estimated at $4483 at week 24 and $8478 at week 56 for female employees and $2959 and $7137 for male employees. When categorized by pain severity, both moderate (NRS 4-6) and severe (NRS 7-10) pain patients' productivity were improved with cost-savings of $1671 (moderate) and $4226 (severe) at week 24. At week 56, productivity benefits continued with cost-savings at $5370 (moderate pain) and $8529 (severe pain).

Conclusions: As assessed by the WPAI instrument, this cost analysis demonstrated extended-release HC/APAP CR improved work productivity after 24 and 56 weeks of treatment in patients with LBP. This analysis may provide useful information to employers and their workers suffering from moderate-severe LBP.

EXAMPLE IV

Impact of Productivity While at Work (Presenteeism) Among Osteoarthritis Patients Taking 12-Hour Extended-Released Hydrocodone/Acetaminophen Tablets at 56 Weeks Methods: As part of a larger clinical trial reported elsewhere, the Work Productivity and Activity Impairment (WPAI) instrument was administered at baseline and weeks 24 and 56 to measure productivity and overall work impairment due to health in patients with moderate-severe chronic pain. The economic impact of improved work productivity and overall work impairment due to health after HC/APAP CR treatment was calculated as the difference in cost (using the 2007 U.S. average weekly wage of $885) from baseline to week 24 and week 56. Analyses by gender and pain intensity (0-10 numeric rating scale, NRS) were also conducted.

Results: Among OA patients, impairment while working due to health decreased from baseline by 12% at week 24 and 15% at week 56. This translates to an average estimated cost-savings per employee of $2549 at week 24, and $7434 at week 56. Overall work impairment due to health decreased from baseline by 11% at week 24 and 15% at week 56. This translates into an average potential savings to employers of $2332 at week 24 and $7254 at week 56. When the study population was stratified by gender, overall work impairment cost-savings were higher in females than in males by $1524 at week 24 and by $1340 at week 56. Categorized by baseline pain severity, severe pain patients (NRS 7-10) had higher cost-savings of $2555 and $3159 at weeks 24 and 56, respectively, compared to patients with moderate baseline pain (NRS 4-6).

Conclusions: This cost analysis, as assessed by WPAI instrument, demonstrated 12-hour extended-release HC/APAP CR improved productivity while at work after 24 and 56 weeks of treatment in patients with OA. This analysis may provide valuable information for employers and their workers suffering from moderate to severe chronic pain.

EXAMPLE V

Assessment of Disability Level and Sleep Interference in Moderate to Severe Chronic Low-Back Pain Patients Treated with 12-Hour Extended-Release Hydrocodone/Acetaminophen Tablets: A Phase-3 Withdrawal Trial Published studies report chronic low-back pain (CLBP) prevalence in the U.S. to be between 4-14%. Beyond pain control, the goal of CLBP treatment also includes improvement in disability level and sleep quality.

Methods: A phase-3 withdrawal study assessing 12-hour extended-release hydrocodone/acetaminophen (HC/APAP CR) treatment in subjects with CLBP, consisted of the following phases: Washout/Screening, 3-week Active-Drug Open-Label (OL), 12-week Double-Blind (DB) in which subjects were randomized to placebo, 1 or 2 tablets HC/APAP CR twice daily, and Taper/Follow-up. Primary endpoint and study design details are reported elsewhere. Additionally, disability level and pain-related sleep interference were assessed and are reported here.

To assess disability levels, subjects were given the Roland-Morris Disability Questionnaire (RMDQ), a 24-item self-administered questionnaire, at OL and DB baselines and final visit. Sleep interference was examined at these time points, with additional assessments at weeks 2, 6, and 12.

Results: During the OL period, improvements in randomized subjects' disability were demonstrated by reductions in RMDQ scores (mean percent change: −52%) from OL-baseline to DB-baseline. Additionally, mean reduction in subject's assessment of pain-related sleep interference score from OL-baseline to end of the OL-period was 4.0 for all subjects randomized into the DB period.

During the DB period, both HC/APAP CR groups demonstrated statistically significantly less mean percent-change increase in RMDQ scores than the placebo group, from DB-baseline to final visit. More specifically, mean percent increase for RMDQ scores in the 1-tablet HC/APAP CR group was 112% compared to 244% in the placebo group (p<0.001). Similarly, statistically significantly less mean increase in sleep interference was observed for the HC/APAP CR groups compared with the placebo group at week 2 (p<0.001), week 6 (p<0.001) and week 12 (p<0.003).

Conclusions: Twice daily administration of both 1 and 2 tablets of HC/APAP CR improved disability scores and decreased pain-related sleep interference relative to placebo.

EXAMPLE VI

Analgesic Efficacy and Safety of Controlled-Release Hydrocodone and Acetaminophen Tablets, Dosed Twice Daily, for Moderate to Severe Mechanical Chronic Low-Back Pain: A Randomized, Double-Blind, Placebo-Controlled Withdrawal Trial Analgesic efficacy and safety of hydrocodone/acetaminophen extended-release (HC/APAP CR) was assessed in subjects with moderate-to-severe chronic low-back pain (CLBP).

Methods: Subjects with CLBP (n=773) were enrolled at 62 sites; study protocol and informed consent were IRB-approved. Study periods were: Washout/Screening, 3-week Active-Drug Open-Label, 12-week Double-Blind in which subjects were randomized to placebo, 1 or 2 tablets HC/APAP CR twice daily, and Taper/Follow-up. Primary efficacy endpoint was mean change from double-blind baseline to final evaluation in Subject's Assessment of CLBP Intensity (VAS). Safety was evaluated by adverse-event (AE) assessment. All results reported are from the Double-Blind period.

Results: 511 subjects were randomized (513 randomized; 511 received ≥1 dose); data for 507 were evaluated for efficacy. Most subjects were women (58%) and white (86%); mean age 48 years. Baseline variables were similar among the 3 groups. Mean change from baseline CLBP intensity was statistically significantly less in subjects in each HC/APAP CR group than in the placebo group (8.6±2.07, 2-tablet; 13.3±2.07, 1-tablet vs 22.2±2.04, placebo; p<0.05). No statistically significant difference was observed between HC/APAP CR groups. For the majority of secondary endpoints, HC/APAP CR 2-tablet treatment demonstrated numerical advantage vs 1-tablet treatment, with statistical superiority for a few analyses. 89/169 (53%) subjects in the HC/APAP CR 2-tablet, 75/170 (44%) in the 1-tablet, and 79/172 (46%) in the placebo group reported ≥1 AE. AEs in ≥5% of subjects in any treatment group were nausea, constipation, diarrhea, headache. Nine subjects reported serious AEs (2 in each HC/APAP CR group; 5 in the placebo group); 28 discontinued due to AEs (3% in the placebo; 6% in the 1-tablet; 7% in the 2-tablet group).

Conclusions: Both HC/APAP CR doses resulted in significantly smaller increases in CLBP intensity vs placebo. The safety profile of HC/APAP CR was consistent with the known profile of a mu-opioid receptor agonist-containing product.

EXAMPLE VII

Effects of 12-Hour, Extended-Release Hydrocodone/Acetaminophen on Pain-Related Work Productivity: A Subanalysis from a 56-Week, Open-Label Study Chronic pain conditions, such as osteoarthritis (OA) and mechanical chronic low back pain (CLBP), among active workers cost employers ~$61.2 billion/yr in lost productive time, which includes both reduced performance while at work and days of work missed (absenteeism). An analysis of lost productivity time from a 56-week, open-label study was conducted to calculate the potential economic effects of treatment with HC/APAP CR to employers.

More specifically, an estimated 50 million Americans suffer with chronic pain, and 41% of patients report that their pain is not adequately controlled. Nicholson B, Ross E, Weil A, Sasaki J, Sacks G. Treatment of chronic moderate-to-severe non-malignant pain with polymer-coated extended-release morphine sulfate capsules. Curr Med Res Opin. Mar 2006;22(3):539-550. Chronic pain is the most common cause of long-term disability and is associated with reduced physical, psychological, and social well-being. Reid M C, Engles-Horton L L, Weber M B, Kerns R D, Rogers E L, O'Connor P G. Use of opioid medications for chronic noncancer pain syndromes in primary care. J Gen Intern Med. March 2002; 17(3):173-179; Longo L P, Parran T, Jr., Johnson B, Kinsey W. Addiction: part II. Identification and management of the drug-seeking patient. Am Fam Physician. Apr. 15 2000;61(8): 2401-2408. Chronic pain conditions, such as osteoarthritis (OA) and mechanical chronic low back pain (CLBP), among active workers cost employers ~$61.2 billion/yr in lost productive time, which is primarily caused by reduced performance while at work as opposed to days of work missed (absenteeism). Stewart W F, Ricci J A, Chee E, et al. Lost Productive Time and Cost Due to Common Pain Conditions in the US Workforce. JAMA. 2003;290:2443-2454. OA is the most common type of arthritis (also known as degenerative joint disease), affecting 12% of adults in the U.S. aged 25 to 74 years. Barnes E V, Edwards N L. Treatment of osteoarthritis. South Med J. February 2005;98(2):205-209; Lawrence R C, Felson, D T, Helmick C G, et al. Estimates of the prevalence of arthritis and other rheumatic conditions in the United States: Part II. Arthritis Rheum. Dec. 28, 2007;58(1):26-35 [Epub ahead of print].

CLBP is back pain that has persisted longer than 3 months, and it affects approximately 19% of working adults in the U.S. Martell B A, O'Connor P G, Kerns R D, et al. Systematic review: opioid treatment for chronic back pain: prevalence, efficacy, and association with addiction. Ann Intern Med. Jan. 16 2007; 146(2):116-127.

First-line pharmacologic treatment for patients with OA or CLBP is typically acetaminophen (APAP) and/or non-steroidal anti-inflammatory drugs (NSAIDs).

For OA and CLBP patients whose pain is not effectively managed by APAP or NSAIDs, combination opioids (codeine, hydrocodone (HC), or oxycodone) may be important treatment alternatives.

Combination opioids, including HC/APAP, have proven effective in the treatment of moderate to severe pain syndromes, such as OA and CLBP, but are currently available only in short-acting formulations.

This study, the first to evaluate the safety and tolerability of any combination opioid product for up to 56 weeks, examined the long-term safety and tolerability of a 12-hour extended-release hydrocodone/acetaminophen (HC/APAP CR) formulation in patients with moderate to severe non-cancer pain, exemplified by OA pain of the hip or knee or CLBP.

Efficacy and safety results are reported in Poster 143. Results reported here are from a selected secondary endpoint of this study that used the Work Productivity and Activity Impairment (WPAI) instrument to calculate the potential economic effects of treatment with HC/APAP CR in a population of patients with moderate to severe pain.

Methods: As part of a larger clinical trial reported elsewhere, the Work Productivity and Activity Impairment (WPAI) instrument was administered at baseline and weeks 24 and 56 to measure reduced productivity and overall work impairment due to health. Results are reported as percentage of lost productivity time and estimated economic impact to employers. Using the 2006 U.S. average weekly wage of $861, the mean costs of reduced productivity and overall work impairment due to health were calculated. The economic impact of improved work productivity and overall work impairment due to health after treatment with HC/APAP CR was calculated as the difference in cost from baseline to week 24 and week 56.

Specifically, this open-label, multicenter study was designed to assess the safety and tolerability of 12-hour 15 mg/500 mg HC/APAP CR tablets administered twice daily in patients with moderate to severe chronic non-malignant pain exemplified by pain of OA of the hip or knee, or CLBP. Reported here are the results from a subanalysis of selected secondary endpoints of pain-related work productivity.

The study was conducted from July 2005 to December 2006.

431 patients were enrolled at 74 study sites. Patients who met the selection criteria were entered into the washout period, and prior analgesic use was discontinued for 5 half lives or 2 days, whichever was longer. Patients returned to the study site and were enrolled in a 7-day titration period if they met the eligibility criteria, including a score of ≥4 on the Subject's Pain Intensity Scale. During the titration period, patients took 1-tablet HC/APAP CR once daily for 3 days, followed by 1-tablet HC/APAP CR twice daily for 4 days.

Following the titration period, patients returned to the study site and were entered into the maintenance period, during which they took 2 tablets of HC/APAP CR twice daily for 56 weeks.

After the maintenance period, patients entered the 1-week study drug taper period, during which patients received 1-tablet HC/APAP CR twice daily for 4 days, followed by 1-tablet once daily for an additional 3 days, after which HC/APAP CR was discontinued (FIG. 8). A follow-up visit was conducted 1 week after study drug discontinuation.

Principal Inclusion Criteria

Patients eligible for participation in the study were between 21 and 75 years of age. Patients met the ACR classification criteria for OA of the hip or the knee or had experienced mechanical low back pain, below the 12th thoracic vertebra for greater than 3 months.

Subject's Pain Intensity Scale by an 11-point Likert scale (0=no pain; 10=worst pain imaginable) was ≥4 at the baseline visit.

Statistical Methods

All costs were represented in 2006 US dollars and computed using SAS v9.1 or v8.2 statistical software.

Efficacy analyses were conducted including all data as observed. That is, no imputations were made for the data that were missing for a scheduled visit.

An efficacy evaluable dataset excluded all 16 patients from a single study center because some of the patients were verbally assisted by study-center personnel in the translation of some portions of the efficacy assessment questionnaires. This population is considered the primary population for reporting summary statistics.

Efficacy Outcomes

The WPAI instrument is a questionnaire used to measure reduced productivity and overall work impairment due to health, and was administered at baseline and at weeks 24 and 56.

Patients were asked to evaluate how much their health problems affected productivity while working and how their health affected their ability to do regular daily activities on a scale of 0-10 (0=no effect, 10=completely prevented work/activity).

Results are reported as a percentage of lost productivity time and estimated economic impact to employers. Using the 2006 U.S. average weekly wage of $861 (reported by the Bureau of Labor Statistics), the mean costs of reduced productivity and overall work impairment due to health were calculated.

The economic impact of improved work productivity and overall work impairment due to health after treatment with HC/APAP CR was calculated as the difference in cost from baseline to week 24 and week 56.

Patient Disposition

A total of 431 patients received at least 1 dose of study drug and were included in the intent-to-treat (ITT) dataset. The majority of ITT patients in the study were female (60%) and white (91%). Mean age was 54 years and age ranged from 21 to 76 years. Summary of baseline characterstics (ITT dataset) and demographics of all patients are presented in Table 5.

TABLE 5

| Demographic Characteristic | HC/APAP CR N = 431 |
| --- | --- |
| Sex [n (%)] | |
| Female | 259 (60) |
| Male | 172 (40) |
| Race [n (%)] | |
| White | 391 (91) |
| Black | 29 (7) |
| Asian | 1 (<1) |
| Other | 10 (2) |
| Age (years) | |
| N | 431 |
| Mean ± SD | 54.0 ± 11.19 |
| Minimum-Maximum | 21.0-76.0 |
| Height$^a$ (cm) | |
| N | 429 |
| Mean ± SD | 169.2 ± 10.16 |
| Minimum-Maximum | 135.0-198.0 |
| Weight$^a$ (kg) | |
| N | 431 |
| Mean ± SD | 91.4 ± 25.20 |
| Minimum-Maximum | 41.0-225.0 |

$^a$At baseline

Results: Pain-related work impairment decreased from baseline by 17.4% at week 24 and 16.6% at week 56. This translates into an estimated cost-savings (per employee) to employers of $3527 at week 24, and $8019 at week 56. Similarly, overall work impairment due to health decreased from baseline by 17.5% at week 24 and 15.8% at week 56. This translates into an average potential savings to employers of $3614 at week 24 and $7596 at week 56. Absenteeism decreased by 1.1% at week 24 and by 0.04% at week 56.

Specifically, WPAI results is as follows:

Impairment while working due to health decreased from baseline by 17.4% at week 24 and 16.6% at week 56. This translates into an estimated cost-savings (per employee) to employers of $3,527 at week 24 and $8,019 at week 56. Similarly, overall work impairment due to health decreased from baseline by 17.5% at week 24 and 15.8% at week 56. This translates into an average potential savings to employers of $3,614 at week 24 and $7,596 at week 56. Work time missed due to health decreased by 1.1% at week 24 and by 0% at week 56. Results are summarized in FIG. 9 and Table 6.

Table 6 depicts the baseline values and mean change from baseline to weeks 24 and 56 in work productivity and activity impairment questionnaire (efficacy evaluable dataset).

TABLE 6

| Mean Change from Baseline to Visit | N | HC/APAP CR Mean ± SD |
|---|---|---|
| Percent work time missed due ot health: Baseline | 130 | 4.6 ± 12.57 |
| Mean Change to Week 24 | 126 | −1.1 ± 16.86 |
| Mean Change to Week 56 | 93 | −0.0 ± 14.22 |
| Mean Change to Final Visit | 130 | 0.1 ± 16.89 |
| Percent impairment while working due to health: Baseline | 128 | 43.5 ± 25.89 |
| Mean Change to Week 24 | 125 | −17.4 ± 28.71 |
| Mean Change to Week 56 | 92 | −16.6 ± 25.60 |
| Mean Change to Final Visit | 128 | −17.2 ± 29.19 |
| Percent overall work impairment due to health: Baseline | 128 | 44.8 ± 26.99 |
| Mean Change to Week 24 | 125 | −17.5 ± 29.93 |
| Mean Change to Week 56 | 92 | −15.8 ± 28.06 |
| Mean Change to Final Visit | 128 | −16.4 ± 30.89 |
| Percent activity impairment due to health: Baseline | 234 | 60.8 ± 24.69 |
| Mean Change to Week 24 | 232 | −24.7 ± 30.63 |
| Mean Change to Week 56 | 166 | −22.3 ± 30.17 |
| Mean Change to Final Visit | 234 | −22.1 ± 31.18 |

Conclusion: As assessed by WPAI instrument, this subanalysis demonstrated 12-hour, extended-release HC/APAP CR improved work productivity after 24 and 56 weeks of treatment in patients with OA and CLBP.

EXAMPLE VIII

Effects of 12-Hour, Extended-Release Hydrocodone/Acetaminophen on Pain-Related Physical Function, Work Productivity, and Sleep Quality: A 56-Week, Open-Label Study Osteoarthritis and mechanical chronic low back pain (CLBP) are common pain conditions that can have a significant negative impact on physical function, work productivity, and sleep quality. Pain reduction is primary treatment, however, improvements in sleep, productivity, and/or maintaining physical functioning are also important. The primary objective was to assess long-term safety and efficacy of extended-release hydrocodone/acetaminophen (HC/APAP CR). Here, we report results from the secondary objectives: sleep, physical function/role, and productivity.

Specifically, osteoarthritis (OA) is the most common type of arthritis (also known as degenerative joint disease), affecting 12% of adults in the U.S. aged 25 to 74 years. CLBP is low back pain that has persisted longer than 3 months and it affects approximately 19% of working adults in the U.S. Reduction of chronic pain was the primary treatment goal in this study. Secondary objectives included sleep, productivity, and/or maintaining physical functioning. First-line pharmacologic treatment for patients with OA or CLBP is typically acetaminophen (APAP) and/or non-steroidal anti-inflammatory drugs (NSAIDs). For OA and CLBP patients whose pain is not effectively managed by APAP or NSAIDs, combination opioids (containing codeine, hydrocodone (HC), or oxycodone) may be important treatment alternatives. Opioids are an important treatment option for moderate to severe chronic pain. Combination opioids, including HC/APAP, have proven effective in the treatment of moderate to severe pain syndromes, such as OA and CLBP, but are currently available only in short-acting formulations.

Methods: Detailed information on the primary endpoint and study design has been reported. Secondary endpoints were assessed using the Brief Pain Inventory (BPI), Work Productivity and Activity Impairment (WPAI), and the SF-36 questionnaires that occurred at baseline, weeks 24 and 56. BPI was also administered at weeks 4, 12, and 40.

Specifically, this open-label, multi-center study was designed to assess the safety and tolerability of 12-hour 15 mg/500 mg HC/APAP CR tablets administered twice daily in patients with moderate to severe chronic non-malignant pain exemplified by pain of OA of the hip or knee, or CLBP.

The study was conducted from July 2005 to December 2006.

431 patients were enrolled at 74 study sites. Patients who met the selection criteria were entered into the washout period, and prior analgesic use was discontinued for 5 half lives or 2 days, whichever was longer.

Patients returned to the study site and were enrolled in a 7-day titration period if they met the eligibility criteria, including a score of ≥4 on the Subject's Pain Intensity Scale. During the titration period, patients took 1-tablet HC/APAP CR once daily for 3 days, followed by 1-tablet HC/APAP CR twice daily for 4 days.

Following the titration period, patients returned to the study site and were entered into the maintenance period, during which they took 2-tablets of HC/APAP CR twice daily for 56 weeks.

After the maintenance period, patients entered the 1-week study drug taper period, during which patients received 1-tablet HC/APAP CR twice daily for 4 days, followed by 1-tablet once daily for an additional 3 days, after which HC/APAP CR was discontinued (FIG. 10). A follow-up visit was conducted 1 week after study drug discontinuation.

Principal Inclusion Criteria

Patients eligible for participation in the study were between 21 and 75 years of age.

Patients met the ACR classification criteria for OA of the hip or the knee or had experienced mechanical low back pain, below the 12th thoracic vertebra for greater than 3 months.

Subject's Pain Intensity Scale by an 11-point Likert scale (0=no pain; 10=worst pain imaginable) was ≥4 at the baseline visit.

Statistical Methods

No statistical tests were performed in this single-arm open-label study. Efficacy analyses were conducted including all data as observed. That is, no imputations were made for data that were missing for a scheduled visit. An efficacy evaluable dataset excluded all 16 patients from a single study center because some of the patients were verbally assisted by study-center personnel in the translation of some portions of the efficacy assessment questionnaires. This population is considered the primary population for reporting summary statistics.

Efficacy Outcomes

Secondary endpoints were assessed using Brief Pain Inventory (BPI), Work Productivity and Activity Impairment (WPAI), and SF-36 questionnaires that were administered at baseline, weeks 24 and 56. BPI was also administered at weeks 4, 12, and 40.

BPI is a validated self-administered 2-page questionnaire used to assess severity and impact of pain on daily functions. In addition, patients rated how pain interfered with general activity, mood, walking ability, normal work, relations with others, sleep, and enjoyment of life during the previous 24 hours. The WPAI instrument is a questionnaire used to measure reduced productivity and overall work impairment due to health. Patients were asked to evaluate how much their health problems affected productivity while working and how their health affected their ability to do regular daily activities.

SF-36 is a questionnaire used to assess patient's own health status at the present time as well as a year prior.

Results: Patients showed improvement in all BPI pain assessments from baseline to each evaluation periods. In particular, patients had less sleep interference (decreased~40-50%) and less interference in walking ability due to pain (decreased~30-40%) from baseline to weeks 4, 12, 24, 40 and 56.

At week 24, impairment while working due to health decreased from baseline by 17.4%, and impairment of regular daily activities decreased 24.7%. At week 56, impairment while working due to health decreased from baseline by 16.6%, and impairment of regular daily activities decreased 22.3%. Overall impairment due to health decreased by 17.5% at week 24 and 15.8% at week 56.

Improvements in all 8-domains of the SF-36 were observed from baseline to study endpoints. Bodily pain, physical role, and physical functioning domains showed the greatest improvements (Mean change: 18.13, 17.46, 14.40, respectively) among the 8-domains at week 24. At final visit, these domains continued to show greatest improvement.

Specifically, a total of 431 patients received at least 1 dose of HC/APAP CR and were included in the intent-to-treat (ITT) data set.

The majority of (ITT) patients in the study were female (60%) and white (91%). Mean age was 54 years and age ranged from 21 to 76 years. Patient demographics and baseline characteristics are summarized in Table 7.

TABLE 7

| Demographic Characteristic | HC/APAP CR N = 431 |
|---|---|
| Sex [n (%)] | |
| Female | 259 (60) |
| Male | 172 (40) |
| Race [n (%)] | |
| White | 391 (91) |
| Black | 29 (7) |
| Asian | 1 (<1) |
| Other | 10 (2) |
| Age (years) | |
| N | 431 |
| Mean ± SD | 54.0 ± 11.19 |
| Minimum-Maximum | 21.0-76.0 |
| Height$^a$ (cm) | |
| N | 429 |
| Mean ± SD | 169.2 ± 10.16 |
| Minimum-Maximum | 135.0-198.0 |

TABLE 7-continued

| Demographic Characteristic | HC/APAP CR N = 431 |
|---|---|
| Weight$^a$ (kg) | |
| N | 431 |
| Mean ± SD | 91.4 ± 25.20 |
| Minimum-Maximum | 41.0-225.0 |

$^a$At baseline

Brief Pain Inventory

Figure 11:
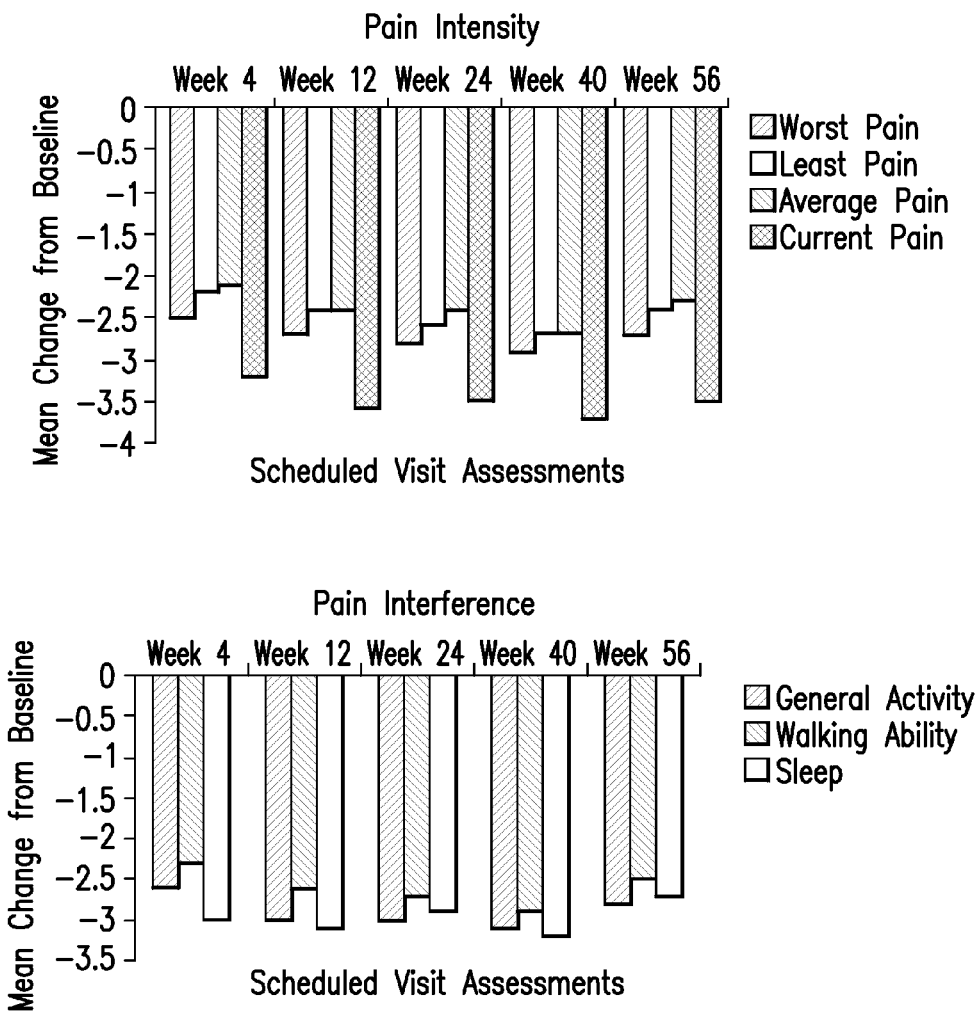
FIG. 11 provides brief pain inventory (BPI) (efficacy evaluable dataset).

Patients showed improvement in all BPI pain assessments from baseline to each scheduled evaluation (FIG. 11).

Particularly for the pain-related interference group, patients had less sleep interference (decreased ~40-50%) and less interference in walking ability due to pain (decreased ~30-40%) from baseline to weeks 4, 12, 24, 40 and 56.

Work Productivity and Activity Impairment Questionnaire (WPAI)

At week 24, impairment while working due to health decreased from baseline 17.4%, and impairment of regular daily activities decreased 24.7%.

At week 56, impairment while working due to health decreased from baseline 16.6%, and impairment of regular daily activities decreased 22.3%.

Overall impairment due to health decreased 17.5% at week 24 and 15.8% at week 56.

SF-36 Health Status Survey

Improvements in all 8 sub-domains, and in the Physical Component Summary (PCS) and the Mental Component Summary (MCS) of the SF-36 were observed from baseline to study endpoints (FIG. 12).

Bodily pain, role-physical, and physical functioning domains showed the greatest improvements (mean change: 18.13, 17.46, 14.40, respectively) among the 8 subdomains at week 24.

At final visit, these domains continued to show greatest improvement.

Conclusion: In this study, OA and CLBP patients taking HC/APAP CR demonstrated improvement in physical function/role and less productivity impairment and pain-related sleep interference.

EXAMPLE IX

Long-Term Efficacy and Tolerability of 12-Hour, Extended-Release Hydrocodone/Acetaminophen: A 56-Week, Open-Label Study Osteoarthritis (OA) and chronic low back pain (CLBP) are 2 of the most prevalent types of chronic, non-cancer pain syndromes in the U.S. Bigos S, Bowyer O, G B. Acute low back problems in adults. Rockville: Agency for Health Care Policy and Research. 1994; Loeser Je. Bonica's Management of Pain. 3rd ed. Lippincott Williams & Wilkins; 2001. OA is the most common type of arthritis (also known as degenerative joint disease) affecting 12% of adults in the U.S. aged 25-74 years. Barnes E V, Edwards N L. Treatment of osteoarthritis. South Med J. February 2005;98(2):205-209; Lawrence R C, Felson, D T, Helmick C G, et al. Estimates of the prevalence of arthritis and other rheumatic conditions in the United States: Part II. Arthritis Rheum. Dec. 28, 2007;58 (1):26-35 [Epub ahead of print] CLBP is low back pain that has persisted longer than 3 months, and it affects approximately 19% of working adults in the U.S. Martell B A, O'Connor P G, Kerns R D, et al. Systematic review: opioid treatment for chronic back pain: prevalence, efficacy, and association with addiction. Ann Intern Med. Jan. 16 2007;146 (2):116-127.

Historically, acetaminophen (APAP) and non-steroidal anti-inflammatory drugs (NSAIDs) have been the first-line pharmacologic therapy used to treat non-cancer pain syndromes, such as OA and CLBP.

For OA and CLBP patients whose pain is not effectively managed by APAP or NSAIDs, combination opioids (containing codeine, hydrocodone (HC), or oxycodone) may be important treatment alternatives.

Opioids are an important treatment option for moderate to severe chronic pain. WHO. The World Health Organization's three step analgesic ladder. Cancer Pain Relief. 1986.

Combination opioids, including HC/APAP, have proven effective in the treatment of moderate to severe pain syndromes, such as OA and CLBP, but are currently available only in short-acting formulations.

An extended-release formulation would potentially increase patient compliance, reduce the occurrence of end-of-dose pain, and improve the overall quality of life of individuals with moderate to severe chronic, non-cancer pain syndromes.

The objective of this study was to evaluate the long-term tolerability and safety of 2 tablets of extended-release hydrocodone 15 mg/acetaminophen 500 mg (HC/APAP CR) administered twice daily in osteoarthritis or mechanical chronic low back pain patients.

Methods: Patients were recruited from 74 US sites. 431 patients enrolled in the titration period and took 1 tablet HC/APAP CR once daily for 3 days followed by 1 tablet twice daily for 4 days. During maintenance, patients took 2 tablets HC/APAP CR twice daily for 56 weeks. Following 56-week maintenance, patients had their medication tapered over one week. Patients received rescue medication (acetaminophen) up to three times per week. Efficacy was evaluated by a pain-intensity Likert Scale, and safety was assessed by adverse event (AE), vital sign and laboratory assessment.

More specifically, this open-label, multicenter study was designed to assess the safety and tolerability of 12-hour 15 mg/500 mg HC/APAP CR tablets administered twice daily in patients with moderate to severe chronic non-malignant pain exemplified by OA pain of the hip or knee, or CLBP.

This study was conducted from July 2005 to December 2006. 431 patients were enrolled at 74 study sites. Patients who met the selection criteria were entered into the washout period, and prior analgesic use was discontinued for 5 half lives or 2 days, whichever was longer.

Patients returned to the study site and were enrolled in a 7-day titration period if they met the eligibility criteria, including a score of ≥4 (out of 10) on the Subject's Pain Intensity Scale. During the titration period, patients took 1-tablet HC/APAP CR once daily for 3 days, followed by 1-tablet HC/APAP CR twice daily for 4 days.

Following the titration period, patients returned to the study site and were entered into the maintenance period, during which they took 2-tablets of HC/APAP CR twice daily for 56 weeks.

After the maintenance period, patients entered the 1-week study drug taper period, during which patients received 1-tablet HC/APAP CR twice daily for 4 days, followed by 1-tablet once daily for an additional 3 days, after which HC/APAP CR was discontinued (FIG. 13). A follow-up visit was conducted 1 week after study drug discontinuation.

Principal Inclusion Criteria

Patients eligible for participation in the study were between 21 and 75 years of age.

Patients met the ACR classification criteria for OA of the hip or the knee or had experienced mechanical low back pain, below the 12$^{th}$ thoracic vertebra for greater than 3 months.

Subject's Pain Intensity Scale by an 11-point Likert scale (0=no pain; 10=worst pain imaginable) was ≥4 at the baseline visit.

Statistical Methods

As the objective of this study was to evaluate the long-term safety and tolerability of HC/APAP CR, no statistical tests were performed in this single arm open-label study.

All demographic, safety, and efficacy analyses were performed using an intent-to-treat (ITT) dataset. All enrolled patients who received 1 dose of study drug were included in the ITT analyses.

An efficacy evaluable dataset excluded all 16 patients from a single study center because some of the patients were verbally assisted by study-center personnel in the translation of some portions of the efficacy assessment questionnaires. This population is considered the primary population for reporting summary statistics.

Rescue Medication

Rescue medication was not permitted 24 hours prior to baseline visit or scheduled study visits; however, patients were permitted to take APAP as rescue medication (not to exceed 2000 mg/day) during the washout, titration, maintenance, and taper periods of the study. All APAP use was recorded in the patient's diary. During titration and maintenance, rescue was limited to 3 days per week.

Efficacy and Safety Outcomes

Pain intensity was evaluated by an 11-point Likert Scale (0=no pain; 10=worst pain imaginable).

Safety was monitored throughout the study based on assessments of adverse events (AEs), physical examinations, vital signs, and laboratory tests.

AEs were coded using the Medical Dictionary for Regulatory Activities (MedDRA) and treatment-emergent AEs were tabulated by system organ class (SOC) and MedDRA preferred term.

For laboratory data, mean changes from baseline were summarized for each laboratory variable.

Results: 415/431 patients comprise the efficacy evaluable dataset reported in the primary analysis population. Pain intensity decreased from baseline at all subsequent evaluations (Table 8A).

TABLE 8A

Mean Change from Baseline to Each Visit

| Pain Intensity Assessment (11-Point Likert Scale) | HC/APAP CR (n = 415) Mean (SD) |
|---|---|
| Baseline | 7.7 (1.39) |
| Change | |
| Week 4 | −2.8 (2.44) |
| Week 12 | −3.0 (2.55) |
| Week 24 | −3.0 (2.72) |
| Week 40 | −3.2 (2.57) |
| Week 56 | −2.7 (2.78) |
| Final visit | −2.6 (2.70) |

The most commonly reported treatment-emergent AEs (≥10% of patients) were constipation, nausea, headache, and somnolence (consistent with previous HC/APAP CR trials). 124 (29%) patients discontinued due to AE(s). The most common (2% of subjects) AEs that led to discontinuation were nausea, somnolence, constipation, dizziness, vomiting, headache, and fatigue. 25 (6%) patients experienced SAE(s); OA (4/431; 1%) was the most common SAE reported. The prevalence of AEs and APAP use decreased after the first 30 days of treatment and remained low over time. There were no reports of hepatotoxicity.

More specifically, the results are described below:

Patient Disposition

A total of 431 patients received at least 1 dose of study drug and were included in the intent-to-treat (ITT) dataset.

The majority of ITT patients in the study were female (60%) and white (91%). Mean age was 54 years and ranged from 21 to 76 years. Summary of demographics of all patients are presented in Table 8.

TABLE 8

| Demographic Characteristic | HC/APAP CR N = 431 |
|---|---|
| Sex [n (%)] | |
| Female | 259 (60) |
| Male | 172 (40) |
| Race [n (%)] | |
| White | 391 (91) |
| Black | 29 (7) |
| Asian | 1 (<1) |
| Other | 10 (2) |
| Age (years) | |
| N | 431 |
| Mean ± SD | 54.0 ± 11.19 |
| Minimum-Maximum | 21.0-76.0 |
| Height$^a$ (cm) | |
| N | 429 |
| Mean ± SD | 169.2 ± 10.16 |
| Minimum-Maximum | 135.0-198.0 |
| Weight$^a$ (kg) | |
| N | 431 |
| Mean ± SD | 91.4 ± 25.20 |
| Minimum-Maximum | 41.0-225.0 |

$^a$At baseline

Time to Discontinuation

57% of the enrolled patients prematurely discontinued the study.

The most frequently reported primary reason for premature discontinuation from the study was an AE (26%; 112/431). An additional 12 patients prematurely discontinued study drug with a secondary reason of treatment-emergent AEs. 124 (29%) patients total discontinued due to AEs. The most common (≥2% of patients) AEs that led to discontinuation were nausea, somnolence, constipation, dizziness, vomiting, headache, and fatigue. Summary of patient disposition information is presented in Table 9.

TABLE 9

| | HC/APAP CR |
|---|---|
| Number of patients planned | 350 |
| All treated patients | 431 |
| Completed study drug treatment; n (%) | 185 (43) |
| Total number of patients prematurely discontinued from study drug; n (%) | 246 (57) |
| Primary Reason for discontinuation from study; n (%) | |
| Adverse event | 112 (26) |
| Withdrew consent | 39 (9) |
| Lack of efficacy | 32 (7) |
| Lost to follow-up | 27 (6) |
| Patient non-compliant | 15 (3) |
| Other | 21 (5) |

Efficacy

415/431 patients comprised the efficacy evaluable dataset reported in the primary analysis population.

Mean reductions in patient's assessment of pain intensity score from baseline were observed beginning at the first evaluation (week 4) and continued at each scheduled evaluation throughout the study.

Figure 14:
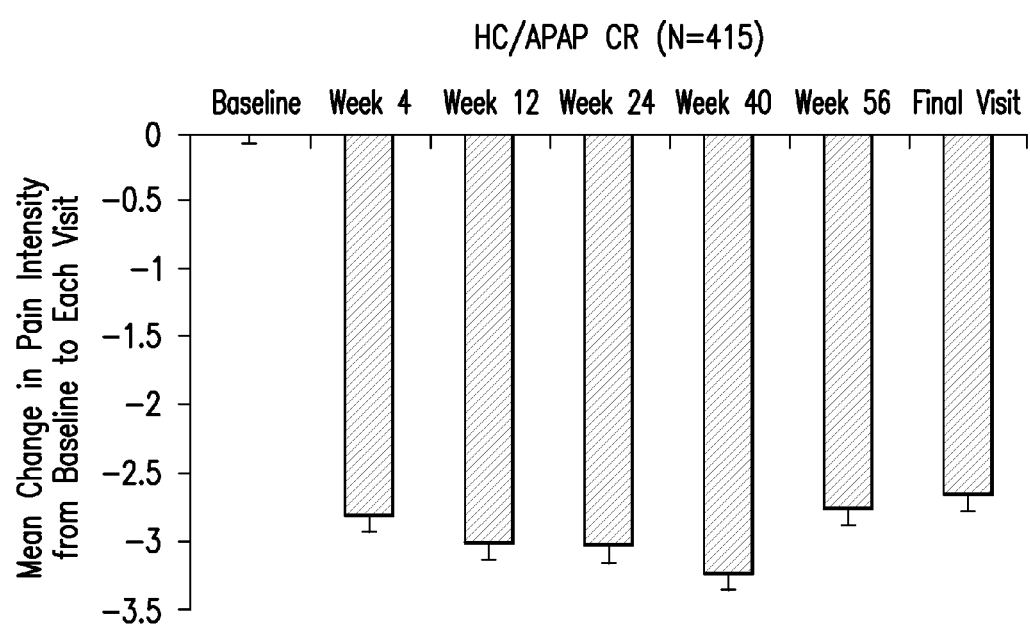
FIG. 14 provides mean reductions in patient's assessment of pain intensity score from baseline–mean values reported±SEM (efficacy evaluable dataset).

Results were similar for the ITT dataset. Efficacy data are summarized in FIG. 14.

Safety

The most commonly reported treatment-emergent AEs (≥10% of patients) were constipation, nausea, headache, and somnolence.

The incidence and prevalence of these common AEs generally decreased over time. Summary of AE information is presented in Table 10.

Table 10 depicts summary of treatment-emergent adverse events occurring in ≥5% of patients in any treatment (ITT dataset).

TABLE 10

| MedDRA Preferred Term | HC/APAP CR (N = 431) n (%) |
|---|---|
| Any Adverse Event | 370 (86) |
| Constipation | 137 (32) |
| Nausea | 111 (26) |
| Headache | 79 (18) |
| Somnolence | 50 (12) |
| Pruritus | 39 (9) |
| Nasopharyngitis | 31 (7) |
| Upper Respiratory Tract Infection | 31 (7) |
| Dizziness | 30 (7) |
| Vomiting | 29 (7) |
| Diarrhea | 28 (6) |
| Insomnia | 27 (6) |
| Fatigue | 25 (6) |
| Back Pain | 24 (6) |
| Anxiety | 20 (5) |
| Depression | 20 (5) |
| Influenza | 20 (5) |

61% of patients reported at least 1 possibly or probably treatment related AE. The most common were constipation, nausea, somnolence, headache, pruritus, dizziness, fatigue, insomnia, vomiting, diarrhea, dry mouth, anxiety, dyspepsia, and sedation.

16% of AEs were considered to be severe. Of the severe AEs, nausea was the most frequently reported. Other severe AEs included constipation, headache, migraine, influenza, depression, vomiting, and OA, but were each reported in ≤2% of patients.

A total of 124 patients (124/431; 29%) reported treatment-emergent AEs that at least in part led to premature discontinuation from the study. The most common (≥2% of patients) treatment-emergent AEs that at least in part led to premature discontinuation from the study were nausea, somnolence, constipation, dizziness, vomiting, headache, and fatigue. All other treatment-emergent AEs that led to premature discontinuation were reported by <2% of patients.

25 (6%) patients reported 1 or more serious AEs (SAEs), none of which were considered by the investigator to be possibly or probably related to study drug.

No clinically meaningful changes from baseline were observed for any laboratory parameter.

There were no reports of hepatotoxicity.

APAP rescue medication use was greatest during the first 30 days and then decreased or remained stable for the duration of the study, suggesting that no tolerance was associated with HC/APAP CR use.

Conclusion: HC/APAP CR was efficacious in the management of chronic non-malignant pain over a duration of 56 weeks. The safety profile of Vicodin CR in this study was consistent with that of a mu-opioid receptor agonist-containing agent. The safety profile of HC/APAP CR was consistent with that of a mu-opioid receptor agonist-containing agent.

EXAMPLE X

Safety and Efficacy of 12-Hour Extended-Release Hydrocodone/Acetaminophen for Acute Pain Following Bunionectomy: A Randomized, Multi-Center Double-Blind Study The safety and efficacy of 1 or 2 tablets of extended-release hydrocodone 15 mg/acetaminophen 500 mg (HC/APAP CR) were evaluated following bunionectomy. Specifically, the primary objective of this study was to compare the analgesic efficacy and safety of HC/APAP CR to placebo in the treatment of moderate to severe pain on the day following primary, unilateral, first metatarsal bunionectomy surgery. The secondary objective was to compare the analgesic efficacy and safety of HC/APAP CR 1 tablet twice daily to placebo in the treatment of moderate to severe pain on the day following primary, unilateral, first metatarsal bunionectomy surgery.

Approximately 25 million people suffer from acute pain resulting from an injury or surgery. Deyo R A, Cherkin D, Conrad D, Volinn E. Cost, controversy, crisis: low back pain and the health of the public. Annu Rev Public Health. 1991; 12:141-156. Due to advances in technology, more surgical procedures are being performed in the ambulatory setting. Ambulatory orthopedic procedures require effective control of postoperative pain. To avoid delayed discharge from the hospital, shorten recovery postsurgery, and improve patient satisfaction in the ambulatory setting, rapid and effective analgesia is crucial for patients with acute postoperative pain. Diaz G, Flood P. Strategies for effective postoperative pain management. Minerva Anestesiol. 2006;72: 145-150; Reuben S S, Connelly N R, Maciolek H. Postoperative analgesia with controlled-release oxycodone for outpatient anterior cruciate ligament surgery. Anesth Analg. 1999;88:1286-1291; Brown A K, Christo P J, Wu C L. Strategies for postoperative pain management. Best Pract Res Clin Anaesthesiol. 2004;18:703-717.

A recent phase 2 study characterized the safety and efficacy of extended-release hydrocodone and acetaminophen (HC/APAP CR) in patients with acute pain following bunionectomy surgery and found that both 1 and 2 tablets BID of HC/APAP CR were significantly superior to placebo (P≤0.05) in reducing pain intensity and providing adequate pain relief after a single dose of the drug was given within 6 hours postsurgery. Desjardins P, Diamond E, Francis C, et al. Treatment of pain with 12-hour controlled release hydrocodone-acetaminophen tablets following acute bunionectomy: A randomized, double-blind, placebo-controlled study, presented at the American Academy of Pain Medicine. New Orleans, La.; 2007.

Postbunionectomy pain is considered a robust and reliable acute pain model to assess analgesic efficacy with multiple doses, 6 and is associated with a predictable level of moderate to severe postoperative pain. Desjardins P J, Black P M, Daniels S, et al. A randomized controlled study comparing rofecoxib, diclofenac sodium, and placebo in post-bunionectomy pain. Curr Med Res Opin. 2004;20:1523-1537.

Methods: 163 patients recruited from 5 US sites were randomized to the following treatment groups: 2 placebo tablets (n=53), 1 tablet HC/APAP CR plus placebo (n=54), or 2 tablets HC/APAP CR (n=56) at onset of moderate to severe pain. Patients were dosed every 12 hours for 48 hours (4 total doses), and after the first dose, were followed for 7 days[±2]. The primary endpoint was time-interval-weighted sum of pain intensity difference (SPID) over the first 12 hours, measured by visual analog scale (VAS), (higher scores indicate better pain relief). Patients received rescue medication as needed.

Specifically, this randomized, multi-center, double-blind, placebo controlled study evaluated the efficacy and safety of 15 mg/500 mg HC/APAP CR, 2 tablets twice daily, in patients with moderate to severe pain following bunionectomy surgery. The study was conducted from January 2007 to April 2007. 163 patients recruited from 5 US sites were randomized to the following treatment groups at onset of moderate to severe pain:

2 placebo tablets (n=53),
1 tablet HC/APAP CR plus placebo (n=54), or
2 tablets HC/APAP CR (n=56)

Figure 15:
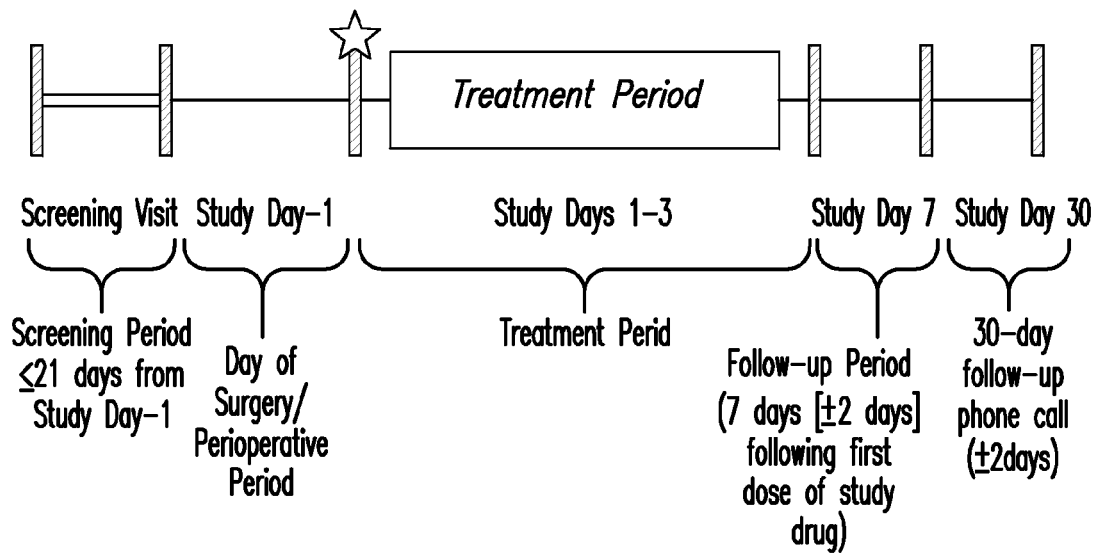
FIG. 15 provides the study design for Example X.

Patients were dosed every 12 hours for 48 hours (4 total doses), and were followed until Study Day 7 [±2 days] after the first dose of study medication. The duration of the study was approximately 4 weeks (FIG. 15).

Principal Inclusion Criteria

Eligible participants were between 18 and 65 years of age, and were in good general health.

Patients were scheduled to undergo primary, unilateral, first metatarsal bunionectomy surgery under regional/local anesthesia and sedation. Patients reported a pain intensity score of ≥40 mm on a 100 mm visual analog scale (VAS, 0=no pain, 100=worst pain imaginable) and had a score of moderate to severe pain on a categorical pain intensity scale on the morning following surgery.

Statistical Analysis

All analyses were conducted using the intent-to-treat (ITT) dataset that included all patients who received at least 1 dose of study drug. For all efficacy and safety end points, the primary comparisons were between the HC/APAP CR 2 tablet-treated group and the placebo treated group. Treatment group mean differences for the primary efficacy variable were evaluated using ANCOVA with factors for treatment group, investigator, and baseline VAS pain intensity score as a covariate.

The time to the patient's perceptible, meaningful, and confirmed pain relief were analyzed using log-rank statistics from nonparametric survival models and Wald statistics from Cox proportional hazards models (with Kaplan-Meier estimates of median time to onset or first use).

For the primary efficacy analysis, all data obtained after subjects received any rescue medication were excluded from the analysis. Missing/excluded pain scores were imputed using last observation carried forward (LOCF) methodology.

Efficacy and Safety Outcomes

The primary endpoint was time-interval weighted sum of pain intensity difference (SPID) over the 0-12 hour interval following study drug administration, measured by VAS (higher scores indicate greater improvement in pain intensity from baseline).

Secondary endpoints were time to patient's perceptible, meaningful, and confirmed pain relief measured in minutes.

Safety was evaluated throughout the study by physical examinations, vital signs, laboratory tests, and adverse events (AEs) monitoring.

Results: 161/163 patients completed the study. Baseline variables were similar among groups. Most patients were female (89%); the mean age was 42.1 years. Patients receiving HC/APAP CR showed statistically significant improvement in all efficacy variables reported here, except 1-tablet HC/APAP CR for perceptible pain relief (Table 11A).

TABLE 11A

Efficacy Results for 0 to 12 Hours

| Variables | Placebo (n = 53) | 1-tablet HC/APAP CR (n = 54) | 2-tablet HC/APAP CR (n = 56) |
|---|---|---|---|
| SPID VAS, mean (SE) | 35.8 (32.5) | 211.8 (32.2)$^a$ | 367.3 (31.6)$^{a,b}$ |
| Pain relief, n (%) | | | |
| Perceptible | 42 (79) | 47 (87) | 55 (98)$^{a,b}$ |
| Meaningful | 27 (51) | 41 (76)$^a$ | 53 (95)$^{a,b}$ |
| Confirmed perceptible | 27 (51) | 40 (74)$^a$ | 52 (93)$^{a,b}$ |

$^a$ p ≤ 0.05 versus placebo
$^b$ p ≤ 0.05 versus 1-tablet

Incidence of adverse events was significantly higher for patients receiving HC/APAP CR versus placebo and for patients receiving 2-tablet HC/APAP CR versus 1 tablet. The most common adverse events were nausea, vomiting, somnolence, headache, dizziness, and pruritus.

Specifically, a total of 163 patients received at least 1 dose of study drug and were included in the ITT analysis (n=53 placebo; n=54 HC/APAP CR 1 tablet; n=56 HC/APAP CR 2 tablets). Baseline demographics were comparable among the 3 treatment groups for race, age, height, and weight. There was a statistically significantly different proportion of men and women among the 3 treatment groups. Most patients were white (80%) and female (88%), and the mean age was 42.1 years (Table 11). Table 11 depicts the demographic and baseline characteristics.

No significant differences (P>0.05) were observed among treatment groups in VAS and categorical pain intensity at Baseline (Table 12). Table 12 depicts the baseline pain intensity.

TABLE 11

| Characteristic | Placebo (n = 53) | HC/APAP CR 1 Tablet (n = 54) | HC/APAP CR 2 Tablets (n = 56) |
|---|---|---|---|
| Sex* (n, %) | | | |
| Female | 42 (79%) | 52 (96%) | 51 (91%) |
| Male | 11 (21%) | 2 (4%) | 5 (9%) |
| Race (n, %) | | | |
| White | 43 (81%) | 43 (80%) | 44 (79%) |
| Black | 8 (15%) | 9 (17%) | 11 (20%) |
| Asian | 2 (4%) | 1 (2%) | 0 (0%) |
| Other | 0 (0%) | 1 (2%) | 1 (2%) |
| Age (mean ± SD) | 41.7 ± 11.47 | 40.8 ± 10.27 | 43.8 ± 11.52 |
| Min-Max | 21-62 | 22-60 | 23-65 |

*p ≤ 0.05

TABLE 12

| Baseline Pain Score | Placebo (n = 53) | HC/APAP CR 1 Tablet (n = 54) | HC/APAP CR 2 Tablets (n = 56) |
|---|---|---|---|
| VAS (0-100 mm) | | | |
| Mean (±SD) | 67.9 ± 12.96 | 66.7 ± 14.01 | 65.3 ± 14.90 |
| Min-Max | 40-96 | 42-98 | 40-100 |
| Categorical Score (n, %) | | | |
| Moderate | 37 (70) | 41 (76) | 42 (75) |
| Severe | 16 (30) | 13 (24) | 14 (25) |

Efficacy
Primary Endpoint

Mean VAS SPID scores for 0 to 12 hours following the initial dose for the HC/APAP CR 1 and 2 tablet-treated groups were significantly greater compared with the placebo-treated group (P<0.001; FIG. 2), indicating greater improvement in pain intensity from baseline.

Mean VAS SPID scores for the HC/APAP CR 2 tablet-treated group were significantly greater compared with the HC/APAP CR 1 tablet treated group (P=0.001; FIG. 16).

Secondary Endpoints

The times to onset of meaningful and confirmed pain relief were significantly less in the HC/APAP CR 1 and 2 tablet-treated groups compared with the placebo-treated group (P≤0.05; Table 3).

A significant difference was also observed between the HC/APAP CR 2 tablet-treated group and the placebo-treated group in the time to perceptible pain relief (P≤0.05; Table 3).

Significantly shorter times to perceptible, meaningful, and confirmed pain relief were observed in the HC/APAP CR 2 tablet-treated group compared with the HC/APAP CR 1 tablet-treated group (P≤0.05; Table 13). Table 13 depicts time to pain relief.

TABLE 13

| Time to Pain Relief (median minutes) | Placebo (n = 53) | HC/APAP CR 1 Tablet (n = 54) | HC/APAP CR 2 Tablets (n = 54) |
|---|---|---|---|
| Perceptible pain relief | 29.0 | 28.0 | 24.0*† |
| Meaningful pain relief | 272.0 | 61.5* | 54.5*† |
| Confirmed pain relief | 67.0 | 30.5* | 24.0*† |

*P ≤ .05 versus placebo
†P ≤ .05 versus HC/APAP CR 1 tablet

Safety

As shown in Table 14, a significantly greater proportion of patients in each of the HC/APAP CR 1 (80%) and 2 (96%) tablet-treated groups experienced at least 1 treatment-emergent AE compared with the placebo-treated group (58%; P≤0.05). Table 14 depicts incidence of treatment-emergent adverse events in ≥5% of patients in any treatment group.

Additionally, a significantly greater proportion of patients in the HC/APAP CR 2 tablet-treated group experienced at least 1 treatment-emergent AE compared with patients in the HC/APAP CR 1 tablet-treated group (P≤0.05).

TABLE 14

| | Treatment Group n (%) | | |
|---|---|---|---|
| MedDRA Preferred Term | Placebo (n = 53) | HC/APAP CR 1 Tablet (n = 54) | HC/APAP CR 2 Tablets (n = 56) |
| Any Adverse Event | 31 (58%) | 43 (80%)* | 54 (96%)*† |
| Nausea | 7 (13%) | 25 (46%)* | 39 (70%)*† |
| Vomiting | 3 (6%) | 10 (19%) | 22 (39%)*† |
| Somnolence | 6 (11%) | 10 (19%) | 17 (30%)* |
| Headache | 9 (17%) | 13 (24%) | 16 (29%) |
| Dizziness | 0 | 14 (26%)* | 13 (23%)* |
| Pruritus | 0 | 6 (11%)* | 9 (16%)* |
| Anorexia | 0 | 3 (6%) | 0 |
| Constipation | 2 (4%) | 5 (9%) | 5 (9%) |
| Diarrhoea | 0 | 1 (2%) | 3 (5%) |
| Pruritus Generalized | 0 | 0 | 3 (5%) |
| Rash | 1 (2%) | 0 | 3 (5%) |

*P ≤ .05 versus placebo
†P ≤ .05 versus HC/APAP CR 1 tablet

Four patients in the HC/APAP CR 2 tablet-treated group prematurely discontinued from the study due to AEs. Each patient prematurely discontinued study drug due to 1 or more AEs (dizziness, vomiting, pruritus, nausea, headache) that were considered by the investigator to be probably related to the study drug.

The majority of AEs in each treatment group were considered by the investigator to be either mild or moderate in severity. Adverse events considered by the investigators to be severe were reported by 26% of patients in the HC/APAP CR 2 tablet-treated group, 28% of patients in the HC/APAP CR 1 tablet-treated group, and 10% of patients in the placebo-treated group.

There were no deaths during the study. Two patients experienced serious AEs (SAEs); both were hospitalized for thromboembolic events considered to be secondary to postoperative immobility. One patient in the HC/APAP CR 1-tablet group experienced a deep vein thrombosis, and a second patient in the 2-tablet group experienced a pulmonary embolism. Neither SAE was considered possibly or probably related to study drug.

Clinical laboratory and vital signs assessments were unremarkable for all treatment groups.

Conclusion: One or 2 tablets of HC/APAP CR provided significantly better pain relief as compared to placebo in patients with moderate to severe acute pain after bunionectomy. Two tablets provided consistently superior pain relief as compared to 1 tablet. The safety data demonstrated an AE profile consistent with that of a mu-opioid-receptor-containing agent.

EXAMPLE XI

Treatment of Acute Pain with 12-Hour Extended-Release Hydrocodone-Acetaminophen Tablets Following Bunionectomy The safety and efficacy of extended-release hydrocodone 15 mg/acetaminophen 500 mg (HC/APAP CR) dosed every 12 hours and short-acting hydrocodone 10 mg/acetaminophen 325 mg (HC/APAP IR) dosed every 4 hours was compared with placebo for moderate-to-severe pain on the day following primary, unilateral, first metatarsal bunionectomy surgery.

Methods: Patients were randomized to one dose of 2 tablets HC/APAP CR (n=26), or 1 tablet HC/APAP IR (n=31) every 4 hours for 3 doses, or placebo (n=31) and assessed for 12 hours. The primary endpoint was the time-interval weighted sum of pain intensity difference (SPID) for 0-12 h following initial drug administration using 100 mm VAS. Secondary endpoints included pain SPID categorical scale (0-12 h), intensity difference (PID), time-interval weighted sum of pain relief (TOTPAR, 0-12 hours) and pain relief and pain intensity difference (SPRID). Safety assessment included adverse event (AE) reports.

Results: Baseline characteristics were similar among treatment groups. Mean SPID (0-12 h) scores were statistically superior for HC/APAP CR (333) and HC/APAP IR (242) versus placebo (20.7). Mean SPID categorical and TOTPAR scores for HC/APAP treatment groups were statistically significantly higher compared with the placebo treatment group. Starting at 1-hour post-dose, mean PID scores for the HC/APAP CR group were statistically significantly greater than placebo and numerically higher than the HC/APAP IR group for all subsequent assessments. At 5 hours, the HC/APAP CR group had significantly greater PID than the HC/APAP IR group. There were no significant differences between each of the HC/APAP treatment groups and placebo in the proportion of patients experiencing AEs. Treatment-emergent AEs experienced by ≥5% in either HC/APAP treatment group were nausea, vomiting, headache, dizziness, somnolence, fatigue, and hypotension. Nausea was the most frequently reported AE and was reported by a statistically significantly greater proportion of patients in the HC/APAP IR treatment group compared with placebo. No serious AEs were reported during the study.

Conclusions: For postoperative pain, HC/APAP CR and HC/APAP IR were significantly superior to placebo in providing effective pain relief. Adverse event rates with each were not statistically significantly higher than with placebo and were consistent with those of a mu-opioid analgesic.

EXAMPLE XII

Effects of 12-Hour Extended-Release Hydrocodone/Acetaminophen Treatment in Cytochrome P450 2D6 Poor Metabolizers Hydrocodone is oxidized to a more potent mu-opioid agonist hydromorphone by cytochrome P450 2D6 (CYP2D6). CYP2D6 poor metabolizers (PMs) cannot convert hydrocodone to hydromorphone, and it is believed that PMs will not gain meaningful analgesia from hydrocodone. Responses of PMs were compared with those of competent metabolizers (non-PMs) during hydrocodone/acetaminophen extended release (HC/APAP CR) treatment following bunionectomy surgery and in osteoarthritis patients, to learn whether CYP2D6 PMs might be effectively treated with HC/APAP CR. DNA samples collected from patients recruited into two multi-center placebo controlled clinical trials were genotyped for major CYP2D6 PM alleles and assigned PM or non-PM status. In a study of acute pain relief after bunionectomy, efficacy variables were assessed descriptively. In a chronic pain study in osteoarthritis, efficacy of HC/APAP CR treatment was evaluated prospectively for the percentage change from baseline to week 12 of pain intensity score (VAS %), using analysis of covariance with a factor for PM status and baseline pain intensity score as a covariate. Other efficacy endpoints were assessed to support the prospective analysis. Tolerability of HC/APAP CR in PMs was assessed descriptively in both studies. Among 130 bunionectomy subjects, four of six PMs dosed with HC/APAP CR experienced meaningful analgesia. Among 276 osteoarthritis subjects, eleven of nineteen PMs dosed with HC/APAP CR experienced meaningful analgesia. No difference was observed between PMs and non-PMs for VAS % (−43.5% v −46.5%, p=0.770). PMs treated with placebo (−21.0%, n=19) did not respond as well as PMs treated with HC/APAP CR. Results for other key efficacy variables were consistent with those for VAS %. Safety-related study dropout and adverse event patterns were similar in PMs and non-PMs in both studies. PMs and non-PMs have similar analgesic responses to HC/APAP CR. This distinguishes HC/APAP CR from tramadol and possibly other opioid-based analgesics.

EXAMPLE XIII

Efficacy and Safety Evaluation of 12 Weeks Extended Release Hydrocodone/Acetaminophen Treatment in Patients with Chronic Low Back Pain (CLBP) by Prior Opioid Use Twice daily 12-hour extended-release hydrocodone 15 mg/acetaminophen 500 mg (HC/APAP CR) demonstrated superior efficacy compared with placebo for the treatment of moderate-to-severe chronic low back pain (CLBP) in a previously reported 12-week randomized, double-blind, placebo-controlled, withdrawal trial. This report evaluates the efficacy and safety of HC/APAP CR by prior opioid use.

Methods: Opioid experienced patients (had taken opioids for CLBP in the last month; 302 of 770 (39%) and opioid naïve patients (had not taken opioids in the last month; 468 of 770 (61%) with CLBP were enrolled at 62 U.S. sites. Study periods were: Washout/Screening, 3-week Active-Drug Open-Label (OL), 12-week Double-Blind (DB) in which patients were randomized to placebo, 1- or 2-tablets HC/APAP CR twice daily, and Taper/Follow-up. The primary efficacy endpoint was mean change from DB-baseline to final evaluation in Subject's Assessment of CLBP Intensity (visual analog scale; 0-100). Safety was evaluated by adverse-event (AE), vital sign and laboratory assessment.

Results: 209/302 (69%) opioid experienced and 302/468 (65%) opioid naïve patients completed the OL period and were randomized to the DB period. For the primary endpoint, both opioid experienced and naïve patient groups receiving HC/APAP CR had smaller mean increases from DB-baseline compared with placebo; this difference was statistically significant for the 2-tablet groups ($p \leq 0.03$). There were no statistically significant differences ($p=0.467$) for the primary endpoint between opioid experienced and naïve patients receiving either placebo, 1-tablet HC/APAP CR or 2-tablets HC/APAP CR. There were no significant differences ($p>0.05$) in overall adverse event rates across treatment groups for either opioid experienced [placebo (51%), 1-tablet HC/APAP CR(43%) or 2-tablets HC/APAP CR (52%)] or opioid naïve patients [placebo (42%), 1-tablet HC/APAP CR (45%) or 2-tablets HC/APAP CR (53%)].

Conclusions: In this study, HC/APAP CR was efficacious for the treatment of moderate-to-severe CLBP and the efficacy and safety profiles were similar for opioid experienced and opioid naïve patients.

EXAMPLE XIV

Safety and Tolerability of Long-Term Extended-Release Hydrocodone/Acetaminophen in Patients with Moderate-to-Severe Noncancer Pain by Prior Opioid Use Twice daily 12-hour extended-release hydrocodone 15 mg/acetaminophen 500 mg (HC/APAP CR) showed efficacy for treatment of moderate-to-severe noncancer pain in a previously reported long-term (56-week), open-label study. This report evaluates safety and efficacy of HC/APAP CR by patients' prior opioid use.

Methods: 431 patients with moderate-to-severe noncancer pain (osteoarthritis/OA or chronic low back pain/CLBP) were recruited from 74 US sites. In the titration period, patients took 1 tablet HC/APAP CR once daily for 3 days followed by 1 tablet twice daily for 4 days. During maintenance, patients took 2 tablets HC/APAP CR twice daily for 56 weeks. Following the maintenance period, patients had their medication tapered over one week. Patients were permitted rescue medication (acetaminophen) up to three times per week. Safety was assessed by adverse event (AE), vital sign and laboratory assessment and efficacy was evaluated by an 11-point pain-intensity scale.

Results: 291 of the 431 (68%) patients entering the study were opioid experienced (had taken opioids in the last month to treat OA or CLBP) and 140 (32%) were opioid naïve. Overall AE rates were significantly higher in opioid naïve patients (92%) compared with opioid experienced patients (83%; $p=0.012$) and the most common AEs were nausea (39% and 19% for naïve and experienced patients, respectively) and dizziness (11% and 5%). A larger percentage of opioid naïve patients discontinued the study primarily due to AEs (32%) compared with opioid experienced patients (23%). At final evaluation, the opioid naïve patient group had greater mean percent improvements in pain intensity from baseline (−33.8) compared with the opioid experienced patient group (−29.7); these differences were not statistically significant ($p=0.435$).

Conclusions: In this long-term study, AE rates were significantly higher in the opioid naïve group compared with the opioid experienced group and similar efficacy was observed for opioid experienced and opioid naïve patients receiving HC/APAP CR.

EXAMPLE XV

HC/APAP CR Tablets have Greater Crushing Force Resistance than Six Other Opioid Formulations The objective was to determine if 15 mg hydrocodone/500 mg acetaminophen extended-release tablets (HC/APAP CR) had a significantly different resistance to crushing force than 5 mg/325 mg hydrocodone/acetaminophen immediate-release tablets (HC/APAP IR) and 10 mg/325 mg HC/APAP IR, 10 mg and 80 mg oxycodone HCl controlled-release tablets (O/HCl CR), and 5 mg and 40 mg oxymorphone hydrochloride extended-release tablets (OPANA ER).

Methods: Medications were crushed or sliced individually on a platen press that could be fitted with one of four different devices: a 4 mm cylindrical platen, a human incisor-shaped platen, a human molar-shaped platen, and a single-edged blade. Pressure for all devices was fixed at 0.3 mm/sec, which approximated a slow chewing speed. For HC/APAP CR, the force (N) necessary to fracture (1) the outer coating alone and (2) the core tablet alone was recorded. For all other tablets, only the force required to fracture the core tablet was recorded. Tablets were tested both "as is" (directly from bottle) and after tablets were pre-soaked for 2 minutes in approximately 1 ml of artificial saliva (Biotene oral balance dry mouth moisturizer, Laclede, Inc.). Results were recorded as kilo Newtons (kN) and relative standard deviations (RSD) expressed as a percentage. Each test condition was repeated 6 times for each medication so statistical inferences could be drawn.

Results: All comparison products were considered to be not statistically similar to HC/APAP CR in resistance to crushing force. The rank order of the breaking strength for the products tested "as is" was HC/APAP CR>O/HCl CR 80 mg>O/HCl CR 10 mg~5/325 HC/APAP IR~10/325 HC/APAP IR~OPANA ER 5 mg~OPANA ER 40 mg. A similar trend was observed for the tablets after presoaking for 2 minutes in artificial saliva. In addition, the force required to fracture the outer coating of the HC/APAP CR tablets was greater than the force required to fracture the comparator tablets.

Conclusions: HC/APAP CR tablets required statistically significantly more crushing force than 5/325 mg and 10/325 mg HC/APAP IR, 10 mg and 80 mg O/HCl CR, and 5 mg and 40 mg OPANA ER tablets.

Example XVI

Safety and Tolerability of Long-Term Extended-Release Hydrocodone/Acetaminophen in Patients With Moderate-to-Severe Noncancer Pain by Prior Opioid Use Twice daily 12-hour extended-release hydrocodone 15 mg/acetaminophen 500 mg (HC/APAP CR) showed efficacy for treatment of moderate-to-severe noncancer pain in a previously reported long-term (56-week), open-label study. This report evaluates safety and efficacy of HC/APAP CR by patients' prior opioid use.

Methods: 431 patients with moderate-to-severe noncancer pain (osteoarthritis [OA] or chronic low back pain [CLBP]) were recruited from 74 US sites. In the titration period, patients took 1 tablet HC/APAP CR once daily for 3 days followed by 1 tablet twice daily for 4 days. During maintenance, patients took 2 tablets HC/APAP CR twice daily for 56 weeks. Following the maintenance period, patients had their medication tapered over one week. Patients were permitted rescue medication (acetaminophen) up to three times per week. Safety was assessed by adverse event (AE), vital sign, and laboratory assessment and efficacy was evaluated by an 11-point pain-intensity scale.

Results: 140 of the 431 (32%) patients entering the study were opioid naïve and 291 (68%) were opioid experienced (had taken opioids in the last month to treat OA or CLBP). Overall AE rates were significantly higher in opioid naïve patients (92%) compared with opioid experienced patients (83%; p=0.012) and the most common AEs were nausea (39% and 19% for naïve and experienced patients, respectively) and dizziness (11% and 5%, respectively). A larger percentage of opioid naïve patients discontinued the study primarily due to AEs (32%) compared with opioid experienced patients (23%). At final evaluation, the opioid naïve patient group had greater mean percent improvements in pain intensity from baseline (−33.8) compared with the opioid experienced patient group (−29.7); these differences were not statistically significant (p=0.435).

Conclusions: In this long-term study, AE rates were significantly higher in the opioid naïve group compared with the opioid experienced group and similar efficacy was observed for opioid naïve and opioid experienced patients receiving HC/APAP CR.

Osteoarthritis (OA) and chronic low back pain (CLBP) are 2 of the most prevalent types of chronic, noncancer pain syndromes in the U.S.[1,2] Acetaminophen (APAP) and non-steroidal anti-inflammatory drugs (NSAIDs) continue to be the first-line pharmacologic therapies used to treat noncancer pain syndromes, such as OA and CLBP. For OA and CLBP patients whose pain is not effectively managed by APAP or NSAIDs, combination opioids (containing codeine, hydrocodone [HC], or oxycodone) may be important treatment alternatives.[3] Combination opioids, including HC/APAP, have proven effective in the treatment of moderate-to-severe pain syndromes, such as OA and CLBP, but are currently available only in short-acting formulations.

An extended-release formulation may potentially increase patient compliance, reduce the frequency of end-of-dose pain, and improve the overall quality of life of individuals with moderate-to-severe chronic, noncancer pain syndromes.

The results of a long-term open-label study demonstrating the 56-week safety and tolerability of extended-release HC/APAP (HC/APAP CR) in the treatment of chronic non-cancer pain in 431 patients with OA or CLBP have been previously reported. Opioids have been shown to be generally effective in both opioid naïve and opioid experienced populations.[5-7] Opioid experienced patients are considered better able to tolerate opioids than opioid naïve patients. In clinical trials, opioid naïve patients generally have higher dropout rates due to adverse events (AEs) than opioid experienced patients. Slow titration is often considered helpful in mitigating these side effects.[8] In this study, a post-hoc, exploratory, subgroup analysis was conducted to determine if safety and tolerability trends of long-term treatment of chronic noncancer pain seen in a recent 56-week multicenter study were preserved when the study population was stratified by opioid use history.

Methods: Study Design

This open-label, multicenter study was designed to assess the safety and tolerability of 12-hour 15 mg/500 mg HC/APAP CR tablets administered twice daily in patients with moderate-to-severe chronic nonmalignant pain exemplified by OA pain of the hip or knee, or CLBP. (FIG. 17.) This study was conducted from July 2005 to December 2006. 431 patients were enrolled at 74 study sites. Patients eligible for inclusion in this analysis were between 21 and 75 years of age; met the ACR criteria for OA of the hip or knee or had experienced mechanical low back pain below the 12th thoracic vertebrae for greater than 3 months; had taken an analgesic for OA or CLBP for the majority of days in the previous 3 months and for at least 4 days/week during the previous 4 weeks prior to screening; and had a Subject's Pain Intensity Scale rating of ≥4 at baseline (0=no pain, 10=worst pain imaginable). Patients must have been an appropriate candidate for around-the-clock opioids as their next step in analgesic management by meeting at least one of the following criteria: Required an opioid (≤40 mg/day oral morphine equivalent, inclusive of breakthrough pain medication), OR Were unable to control pain with non-opioid analgesics, or such analgesics were contraindicated. Patients who met the selection criteria were entered into the washout period, and prior analgesic use was discontinued for 5 half-lives or 2 days, whichever was longer. Patients returned to the study site and were enrolled in a 7-day titration period (with an optional second week of titration) if they met the eligibility criteria, including a score of ≥4 (out of 10) on the Subject's Pain Intensity Scale. During the titration period, patients took 1-tablet HC/APAP CR once daily for 3 days, followed by 1-tablet HC/APAP CR twice daily for 4 days. Following the titration period, patients returned to the study site and were entered into the maintenance period, during which they took 2-tablets of HC/APAP CR twice daily for 56 weeks. After the maintenance period, patients entered the 1-week study drug taper period, during which patients received 1-tablet HC/APAP CR twice daily for 4 days, followed by 1-tablet once daily for an additional 3 days, after which HC/APAP CR was discontinued. (FIG. 17.) A follow-up visit was conducted 1 week after study drug discontinuation.

Rescue medication was not permitted within 24 hours prior to baseline visit or scheduled study visits; however, patients were permitted to take APAP as rescue medication (not to exceed 2000 mg/day) during the washout, titration, maintenance and taper periods of the study. All APAP use was recorded in the patient's diary. During titration and maintenance, rescue was limited to 3 days per week. Post-hoc analyses controlling for opioid use history were performed. All demographic and safety analyses were performed using an intent-to-treat (ITT) dataset. All enrolled patients who received 1 dose of study drug were included in the ITT analyses. The efficacy evaluable dataset excluded all 16 patients from a single study center because some of the patients were verbally assisted by study center personnel in the translation of some portions of the efficacy assessment questionnaires. Patients were designated to be opioid naïve or opioid experienced by answering no or yes to the following question: "Has the subject previously received opioid therapy to treat his/her OA pain or low back pain?"

Safety and Efficacy Outcomes

Safety was monitored throughout the study based on assessments of adverse events (AEs), physical examinations, vital signs and laboratory tests.

AEs were coded using the Medical Dictionary for Regulatory Activities (MedDRA) and treatment-emergent AEs were tabulated by system organ class (SOC) and MedDRA preferred term. Efficacy was evaluated by pain intensity on an 11-point Likert Scale (0=no pain; 10=worst pain imaginable).

Baseline Demographics

A total of 140 (32%) patients entering the study were opioid naïve and 291 of the 431 (68%) were opioid experienced. (Table 15.) Table 15 depicts demographics and baseline characteristics by opioid use.

TABLE 15

|  | Opioid Naïve N = 140 | Opioid Experience N = 291 | Total Population N = 431 |
|---|---|---|---|
| Sex [n %] | | | |
| Female | 83 (59) | 176 (60) | 259 (60) |
| Male | 57 (41) | 115 (40) | 172 (40) |
| Race [n %] | | | |
| White | 126 (90) | 265 (91) | 391 (91) |
| Black | 11 (8) | 18 (6) | 29 (7) |
| Asian | 0 (0) | 1 (<1) | 1 (<1) |
| Other* | 3 (2) | 7 (2) | 10 (2) |
| Age (years) | | | |
| Mean ± SD | 54.5 ± 11.31 | 53.7 ± 11.15 | 54.0 ± 11.19 |
| Minimum-Maximum | 21-75 | 23-76 | 21-76 |
| Weight (kg)† | | | |
| Mean ± SD | 90.8 ± 26.12 | 91.7 ± 24.79 | 91.4 ± 25.20 |
| Minimum-Maximum | 43-219 | 41-225 | 41-225 |
| Baseline Pain Intensity | | | |
| Mean ± SD | 7.4 ± 1.38 | 7.7 ± 1.40 | 7.6 ± 1.40 |
| Minimum-Maximum | 4-10 | 4-10 | 4-10 |

*Includes "Native American" and mixed races.
†At baseline

No statistically significant differences in baseline demographics were observed between opioid naïve and opioid experienced patients.

Safety and Tolerability

In the overall population, the most commonly reported treatment-emergent AEs (≥10% of patients) were constipation, nausea, headache and somnolence. (Table 16.) When adverse events were analyzed by opioid use history, significantly more patients experienced adverse events in the opioid naïve subgroup (92%) compared to the opioid experienced subgroup (83%). When adverse events were analyzed by opioid use history, opioid naïve patients had a significantly greater incidence of nausea and dizziness. Table 16 depicts treatment-emergent adverse events ≥5% by opioid use.

TABLE 16

|  | Opioid Naïve N = 140 (%) | Opioid Experienced N = 291 (%) | Total Population N = 431 (%) |
|---|---|---|---|
| Any AE | 129 (92)* | 241 (83) | 370 (86) |
| Constipation | 48 (34) | 89 (31) | 137 (32) |
| Nausea | 55 (39)* | 56 (19) | 111 (26) |
| Headache | 22 (16) | 57 (20) | 79 (18) |
| Somnolence | 19 (14) | 31 (11) | 50 (12) |
| Pruritus | 17 (12) | 22 (8) | 39 (9) |
| Nasopharyngitis | 9 (6) | 22 (8) | 31 (7) |
| Upper Respiratory Tract Infection | 10 (7) | 21 (7) | 31 (7) |
| Dizziness | 15 (11)* | 15 (5) | 30 (7) |
| Vomiting | 12 (9) | 17 (6) | 29 (7) |
| Diarrhea | 7 (5) | 21 (7) | 28 (6) |

TABLE 16-continued

|  | Opioid Naïve N = 140 (%) | Opioid Experienced N = 291 (%) | Total Population N = 431 (%) |
|---|---|---|---|
| Insomnia | 13 (9) | 14 (5) | 27 (6) |
| Fatigue | 10 (7) | 15 (5) | 25 (6) |
| Back Pain | 6 (4) | 18 (6) | 24 (6) |
| Anxiety | 10 (7) | 10 (3) | 20 (5) |
| Depression | 5 (4) | 15 (5) | 20 (5) |
| Influenza | 10 (7) | 10 (3) | 20 (5) |

*p ≤ 0.05 for pairwise comparisons between opioid use history groups using Fisher's exact test There was no statistically significant difference in the overall premature discontinuation rates between opioid naïve and opioid experienced patients. (Table 17.) Statistically significantly more opioid naïve patients prematurely discontinued the study primarily due to adverse events (32%) than did opioid experienced patients (23%, p=0.046). Table 17 depicts patient disposition by opioid use.

TABLE 17

|  | Opioid Naïve N = 140 | Opioid Experienced N = 291 | Total Population N = 431 |
|---|---|---|---|
| Completed drug treatment, n (%) | 58 (41) | 127 (44) | 185 (43) |
| Prematurely discontinued drug treatment, n (%) | 82 (59) | 164 (56) | 246 (57) |
| Primary reason for discontinuation of drug treatment, n (%) | | | |
| Adverse event | 45 (32)* | 67 (23) | 112 (36) |
| Withdrew consent | 10 (7) | 29 (10) | 39 (9) |
| Lack of efficacy | 6 (4) | 26 (9) | 32 (7) |
| Lost to follow-up | 7 (5) | 20 (7) | 27 (6) |
| Patient non-compliant | 8 (6) | 7 (2) | 15 (3) |
| Other | 6 (4) | 15 (5) | 21 (5) |

*p ≤ 0.046 for pairwise comparison between opioid use history groups using Fisher's exact test.

In the overall population, twenty-five (6%) patients reported 1 or more serious AEs (SAEs), none of which were considered by the investigator to be possibly or probably related to study drug. No clinically important trends in serious adverse events were seen either within or between opioid use history subgroups. Differences in serious adverse events (SAEs) analyzed by opioid use history were not statistically significant (p=0.509). A total of 10 of 140 (7%) opioid naïve patients and 15 of 291 (5%) opioid experienced patients had at least 1 SAE.

Efficacy

Figure 18:
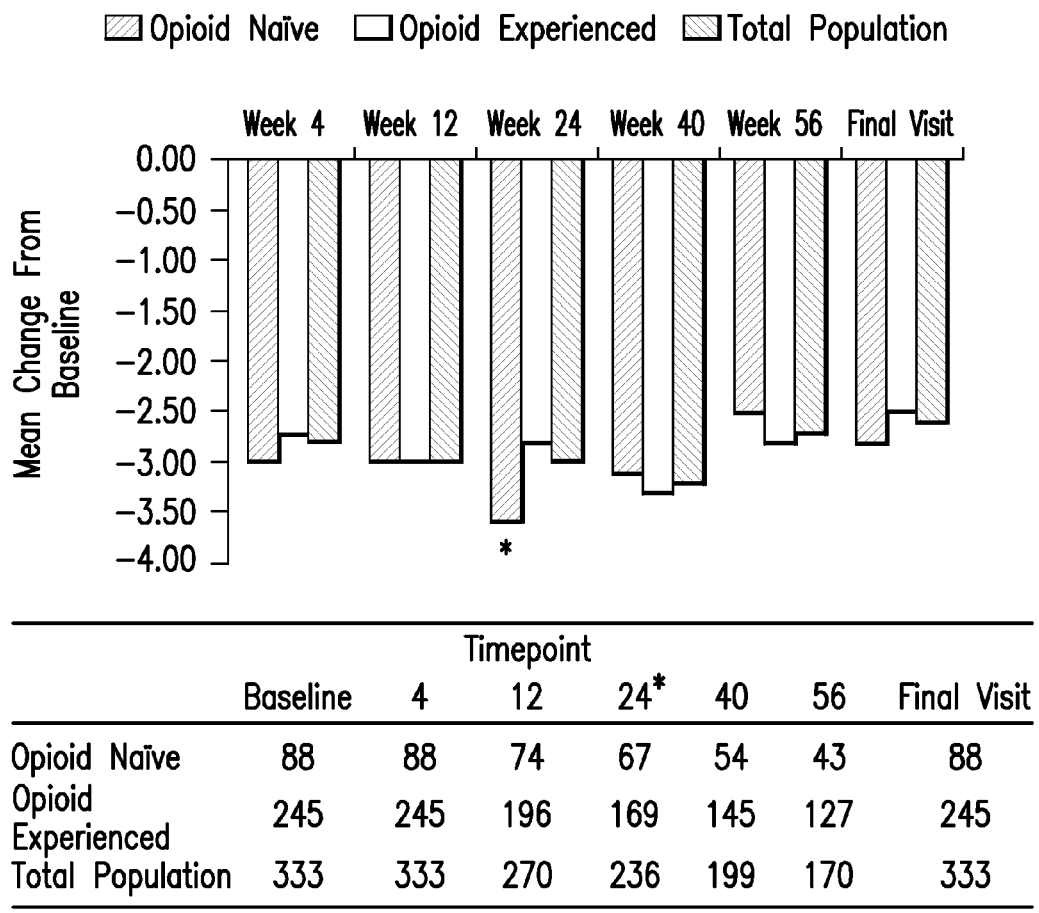
FIG. 18 provides mean reductions in patient's assessment of pain intensity score from Baseline (Observed Cases: Efficacy Evaluable Set)

Mean reductions in patient's assessment of pain intensity score from baseline were observed beginning at the first evaluation (week 4) and continued at each scheduled evaluation throughout the study. At final evaluation, the opioid naïve patient group had greater mean percent improvements in pain intensity from baseline (−33.8%) compared with the opioid experienced patient group (−29.7%); these differences were not statistically significant (p=0.435). At all but one visit, there were no statistically significant differences in efficacy between opioid naïve and opioid experienced patients. (FIG. 18.) FIG. 18 depicts mean reductions in patient's assessment of pain intensity score from baseline (observed cases: efficacy evaluable set)

The overall results of this first study examining the long-term safety and tolerability of HC/APAP CR indicate that: The safety profile of HC/APAP CR in this study was consistent with that of a mu-opioid receptor agonist-acetaminophen containing agent.

HC/APAP CR was efficacious in the management of moderate to severe chronic, nonmalignant pain over a period of 56 weeks. When evaluating safety and efficacy by opioid use history. The number of patients reporting at least one adverse event (particularly nausea and dizziness) was statistically significantly higher in opioid naïve patients compared with opioid experienced patients. Overall premature discontinuation rates were similar between opioid naïve and opioid experienced patients, but overall premature discontinuation rates due to adverse events were statistically significantly higher in opioid naïve patients compared with opioid experienced patients. Similar efficacy was observed for opioid naïve and opioid experienced patients with severe, chronic, nonmalignant pain receiving HC/APAP CR over a period of 56 weeks.

The present invention generally provides a method of treatment and improvement of quality of life for patients adversely affected by various pain conditions. One preferred embodiment provides a method of treatment of acute pain, moderate to moderately severe pain, chronic pain, non-cancer pain, osteoarthritic pain, bunionectomy pain or lower back pain in a patient in need thereof, comprising providing at least one or two dosage form having about 15 mg of hydrocodone and its salt and about 500 mg of acetaminophen, once, twice or thrice daily. Preferably, the dosage form is about 30 mg of hydrocodone and about 1000 mg of acetaminophen taken twice daily. Alternatively, the dosage form is about 15 mg of hydrocodone and about 500 mg of acetaminophen taken twice daily. Also, preferably, these dosage forms may be taken by the patient with or without food. In another aspect of the invention, co-administration of about 240 ml of 40%, 20%, 4% and 0% ethanol on the single dosage form affects the mean maximum plasma concentration level Cmax by ≤25% for both hydrocodone and acetaminophen in the patient. In another aspect, the Cmax and the AUC of hydrocodone for a patient with mild to moderately impaired hepatic function is substantially similar to the normal patient and the Cmax and the AUC of acetaminophen for a patient with mildly impaired hepatic function is substantially similar to the normal patient. Also, no overall statistical differences in effectiveness is observed for the patient metabolizing hydrocodone when the patient is a poor or competent metabolizer of Cytochrome P450 2D6 polymorphism.

Another embodiment of the invention provides a method of improving quality of life in a patient in need thereof, comprising administering to said patient a controlled release twice daily dosage form including acetaminophen and hydrocodone or a therapeutically effective salt thereof. In yet another embodiment, the invention provides a method of reducing loss of productivity in a patient having pain related condition, comprising administering to said patient a controlled release twice daily dosage form including acetaminophen and hydrocodone or a therapeutically effective salt thereof. Preferably, the dosage form comprises about 15 mg of hydrocodone or a therapeutically acceptable salt thereof and about 500 mg of acetaminophen. Or preferably, in all above embodiments, the dosage form comprises about 15 mg of hydrocodone or a therapeutically acceptable salt thereof and about 500 mg of acetaminophen. Alternatively, the dosage form comprises about 30 mg of hydrocodone or a therapeutically acceptable salt thereof and about 1000 mg of acetaminophen.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

The invention claimed is:

1. A method of treating osteoarthritic pain, or lower back pain in a patient in need thereof, wherein the method comprises administering at least one or two dosage form to the patient comprising about 30 mg of hydrocodone and its salt and about 1000 mg of acetaminophen, once, twice or thrice daily, wherein the dosage form comprises a monoeximic pharmaceutical composition, wherein hydrocdone Cmax is less than 25 ng/ml, and wherein co-administration of about 240 ml of 40%, 20%, 4% and 0% ethanol on the single dosage form affects the mean maximum plasma concentration level Cmax by ≤25% for both hydrocodone and acetaminophen in the patient.

2. The method according to claim 1, wherein said dosage form may be taken by the patient with or without food.

3. The method according to claim 1, wherein no overall statistical differences in effectiveness is observed for the patient metabolizing hydrocodone when the patient is a poor or competent metabolizer of Cytochrome P450 2D6.

4. The method according to claim 1, wherein administration of the dosage form improves a quality of life in the patient.

5. The method according to claim 1, wherein administration of the dosage form reduces loss of productivity in the patient.

* * * * *